US009688766B2

(12) United States Patent
Takahashi et al.

(10) Patent No.: US 9,688,766 B2
(45) Date of Patent: *Jun. 27, 2017

(54) STABILIZED HUMAN IGG4 ANTIBODIES

(71) Applicant: KYOWA HAKKO KIRIN CO., LTD, Tokyo (JP)

(72) Inventors: Nobuaki Takahashi, Tokyo (JP); Hideaki Yoshida, Gunma (JP)

(73) Assignee: KYOWA HAKKO KIRIN CO., LTD, Tokyo (JP)

(*) Notice: Subject to any disclaimer, the term of this patent is extended or adjusted under 35 U.S.C. 154(b) by 169 days.

This patent is subject to a terminal disclaimer.

(21) Appl. No.: 14/539,486

(22) Filed: Nov. 12, 2014

(65) Prior Publication Data

US 2015/0141621 A1    May 21, 2015

Related U.S. Application Data

(63) Continuation of application No. 11/663,340, filed as application No. PCT/JP2005/017463 on Sep. 22, 2005, now Pat. No. 8,911,726.

(30) Foreign Application Priority Data

Sep. 22, 2004  (JP) ................................ 2004-275908

(51) Int. Cl.
| | |
|---|---|
| *A61K 39/395* | (2006.01) |
| *C07K 16/28* | (2006.01) |
| *C12N 15/13* | (2006.01) |
| *C07K 16/00* | (2006.01) |

(52) U.S. Cl.
CPC .... *C07K 16/2878* (2013.01); *A61K 39/39591* (2013.01); *C07K 16/00* (2013.01); *C07K 2316/96* (2013.01); *C07K 2317/21* (2013.01); *C07K 2317/24* (2013.01); *C07K 2317/52* (2013.01); *C07K 2317/56* (2013.01); *C07K 2317/76* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 6,376,653 B1 | 4/2002 | Holmes et al. | |
| 6,936,698 B2 | 8/2005 | Taylor | |
| 6,998,124 B1 | 2/2006 | Erickson-Miller et al. | |
| 7,193,064 B2 | 3/2007 | Mikayama et al. | |
| 8,911,726 B2 * | 12/2014 | Takahashi | A61K 39/39591 424/130.1 |

| | | | |
|---|---|---|---|
| 2002/0062009 A1 | 5/2002 | Taylor | |
| 2003/0059427 A1 | 3/2003 | Force et al. | |
| 2004/0120948 A1 | 6/2004 | Mikayama et al. | |
| 2006/0074225 A1 | 4/2006 | Chamberlain et al. | |

FOREIGN PATENT DOCUMENTS

| | | |
|---|---|---|
| EP | 1 391 464 A1 | 2/2004 |
| JP | 2002-512776 | 5/2002 |
| WO | 02/088186 | 11/2002 |
| WO | 03/074679 A2 | 9/2003 |

OTHER PUBLICATIONS

Japanese Office Action issued in Application No. 2006-536409, dated Jan. 4, 2011.
J.R.L, Pink, et al; "Human Immunoglobulin Subclass"; Biochem J.; 1970; vol. 117 pp. 33-47.
Japanese Office Action, issued by the Japanese Patent Office in corresponding Japanese Application No. 2006-536409 on Jan. 10, 2012.
Newman, Roland et al., "Modification of the Fc Region of a Primatized IgG Antibody to Human CD4 Retains Its Ability to Modulate CD4 Receptors but Does Not Deplete CD4 T Cells in Chimpanzees," Clinical Immunology, vol. 98, No. 2, Feb. 2001, pp. 164-174.0.
Dall'Acqua et al., Biochemistry 37: 9266-9273, 1998.
Supplementary European Search Report EP 05 78 5180, Nov. 21, 2008.
F. Ciccimarra et al., "Localization of the IgG Effector Site for Monocyte Receptors", Proc. Nat. Acad. Sci. USC, vol. 72, No. 6, pp. 2081-2083, Jun. 1975.
Lionel S. Zuckier et al., "Chimeric Human-Mouse IgG Antibodies with Shuffled Constant Region Exons Demonstrate that Multiple Domains Contribute to in Vivo Half-Life", Cancer Research 58, 3905-3908—Sep. 1, 1998.
Rob C. Aalberse et al., "IgG4 breaking the rules," Immunology 2002 105, 9-19.
Emmanuelle Bonnin et al., "Generation of functional scFv intrabodies for triggering anti-tumor immunity", Methods 34 (2004) 225-232.
A. Brusco et al., "Molecular charactrization of immunoglobulin G4 gene Isoallotypes", European Journal of Immunogenetics 25, pp. 349-355. 1998.

* cited by examiner

*Primary Examiner* — Phillip Gambel
(74) *Attorney, Agent, or Firm* — Sughrue Mion, PLLC

(57) ABSTRACT

A highly stable mutant of human IgG4 antibody is provided. Such antibody is an antibody in which the CH3 domain of human IgG4 is substituted with the CH3 domain of human IgG1 and which exhibits inhibited aggregate formation, an antibody in which the CH3 and CH2 domains of human IgG4 are substituted with the CH3 and CH2 domains of human IgG1, respectively, or an antibody in which arginine at position 409 indicated in the EU index proposed by Kabat et al. of human IgG4 is substituted with lysine and which exhibits inhibited aggregate formation.

17 Claims, 7 Drawing Sheets

STABILIZED HUMAN IGG4 ANTIBODIES

CROSS REFERENCES

This is a continuation application of U.S. application Ser. No. 11/663,340 (now allowed), filed Aug. 24, 2007, which is a national stage entry of PCT/JP2005/01746, filed Sep. 22, 2005, which claims priority from JP 2004-275908, filed Sep. 22, 2004; the entire contents of all of which are incorporated herein by reference in their entirety.

TECHNICAL FIELD

The present invention relates to an IgG4 mutant having improved physical properties, which is obtained by introducing mutation into a constant region of human IgG4.

BACKGROUND ART

Immunoglobulins are glycoproteins that exist in serum and tissue/body fluid of all mammals. Immunoglobulins have a function of recognizing foreign antigens. Immunoglobulins are involved in biological defense through activation of their effector functions. Effector functions involve activation of the complement system, which is induced by antibody-antigen binding, and effects of promoting cell phagocytosis, antibody-dependent cellular cytotoxicity, mediator release, and antigen presentation Fc receptors (FcR) that exist on the cell surface.

There are 5 different classes of human immunoglobulins, namely IgG, IgA, IgM, IgD, and IgE. IgG can be classified into the 4 subclasses of IgG1, IgG2, IgG3, and IgG4. Also, IgA can be classified into the 2 subclasses of IgA1 and IgA2. The basic structure of immunoglobulin is made up of 2 homologous L chains (light chains) and 2 homologous H chains (heavy chains). The immunoglobulin class and subclass are determined by H chains.

Different immunoglobulins are known to have different functions. For instance, the level of complement-binding ability is ranked in the following order: IgM>IgG3>IgG1>IgG2. Also, the level of affinity to Fc7RI (Fc receptor I) is ranked in the following order: IgG3>IgG1>IgG4>IgG2. In addition, IgG1, IgG2, and IgG4 can bind to protein A.

Human antibodies that have been collected and purified from blood are used as pharmaceutical agents. In recent years, many monoclonal antibodies have been subjected to clinical tests. Also, many such antibodies have been placed on the market. However, most of the monoclonal antibodies used as pharmaceutical agents that have been placed on the market or clinically developed are derived from IgG1. Very few such antibodies are derived from IgG4. It has been known that IgG4 is characterized by having lower levels of complement activation and antibody-dependent cellular cytotoxicity than IgG1. Thus, it is considered that IgG4-derived products are appropriate for use as pharmaceutical agents having such characteristics. Upon activation of the effector function of an antibody that is bound to an antigen, a cell expressing the antigen is damaged via a complement system or another cell. In a case in which such antigen is a cancer-specific antigen or the like, the function of cell damage is very important in terms of medicinal properties. However, in the cases of some antigens, such function might cause adverse effects. An example of such antigen is CD40. The CD40 gene plays an important role in immune control. Anti-CD40 antibodies that inhibit binding between a CD40 ligand and CD40 are considered to have high potential as pharmaceutical agents. However, CD40 expression is found in various other types of cells besides immunocytes. Therefore, if the effector function of such an antibody causes damage to a CD40-expressing cell, there is a possibility that severe adverse effects could be induced. Thus, IgG4 is considered to be a preferable antibody against such aforementioned antigens.

Meanwhile, in order to produce IgG4 that serves as a pharmaceutical agent, certain problems must be considered. Such problems involve the existence of an IgG4 half antibody having no SS bond between its H chains in vivo. (An antibody generally comprises 2 L chains and 2 H chains; however, a half antibody comprises a single L chain and a single H chain.) Also, problematic is the production of a half antibody in a case in which IgG4 is expressed in animal cells such as CHO for the production of a pharmaceutical agent. Such half-antibody formation is a serious problem that is a cause for concern in terms of the production of pharmaceutical agents. However, it has been reported that half-antibody formation can be inhibited by introducing a single amino acid substitution into a constant region (see Non-Patent Document 1). In addition, although IgG4 is known to have a lower level of antibody-dependent cellular cytotoxicity compared with IgG1, IgG4 has FcR-binding ability, although at a weak level. However, such FcR-binding ability can be further attenuated by introducing a mutation into a hinge region of IgG4 so as to improve IgG4 (see Patent Documents 1 to 3).

In accordance with the methods described above, it becomes possible to produce almost ideal IgG4. However, in terms of production of a pharmaceutical agent comprising IgG4, there are still problems to be overcome. Such problems involve instability of IgG4 antibodies at low pH. In general, a method of affinity purification with the use of protein A is used to produce antibodies as pharmaceutical agents. In such case, a low-pH buffer is often used for elution of antibodies each binding to protein A. In addition, in order to remove viruses, it is desired that antibodies be treated at low pH for a certain period of time. However, as shown in the present invention, it has been known that IgG4 antibodies are likely to form an aggregate since they have poor stability at low pH compared with IgG1 antibodies. It has been reported that incorporation of an aggregate into a pharmaceutical agent causes promotion of infusion reactions, complement activation, or antibody-dependent cellular cytotoxicity. Thus, it is easily assumed that such reactions and the like give rise to adverse effects. Therefore, it is very important to reduce the amount of aggregate as less as possible.

[Patent Document 1] JP Patent No. 3101690
[Patent Document 2] U.S. Pat. No. 5,648,260
[Patent Document 3] U.S. Pat. No. 5,624,821
[Non-Patent Document 1] S. Angal et al., Molecular Immunology 1993, 30, 105-108

DISCLOSURE OF THE INVENTION

It is an objective of the present invention to produce a highly stabilized mutant of human antibody IgG4.

As a result of intensive studies, the present inventors succeeded in producing a human IgG4 mutant in which antibody activity is maintained and physical properties are improved compared with known human IgG4. This has led to the completion of the present invention. The basic idea of modification of human IgG4 in the present invention will hereafter be described in detail.

In the heavy chain constant region of human IgG4, at least a CH3 domain is substituted with a CH3 domain of the heavy chain constant region of human IgG1. Alternatively, in the heavy chain constant region of human IgG4, at least CH2 and CH3 domains are substituted with CH2 and CH3 domains of human IgG1, respectively. Thus, antibody stability can be improved. In addition, arginine (R) at position 409 of human IgG4 is substituted with lysine (K), threonine (T), methionine (M), or leucine (L) (e.g., substitution of arginine (R) at position 409 with lysine (K), hereafter referred to as "R409K" in some cases) such that antibody stability can be improved. (Each alphabetical letter stands for a corresponding amino acid and each number is a number according to the EU index proposed by Kabat et al. (Kabat et al., Sequences of proteins of Immunological Interest, 1991 Fifth edition).)

Further, if it is possible to substitute D270, K322, P329, or P331 with A or to convert P331 to S or G, CDC activity can be reduced.

Likewise, if it is possible to substitute L235 with E and G237 with A, ADCC activity can be reduced.

Furthermore, the present invention encompasses a fusion protein comprising a portion containing at least a CH3 domain that exists in a heavy chain constant region of human IgG4 in which at least arginine (R) at position 409, which is indicated in the EU index as in Kabat et al., is substituted with lysine (K), threonine (T), methionine (M), or leucine (L). Preferably, such portion further comprises a hinge region and a CH2 domain.

Specifically, the present invention will be as described below.

[1] An antibody, wherein at least arginine at position 409 in a heavy chain constant region of human IgG4, which is indicated in the EU index as in Kabat et al., is substituted with lysine, threonine, methionine, or leucine, and several amino acid is further deleted from, subjected to substitution in, inserted into, or added to such heavy chain constant region.

[2] The antibody according to [1], wherein serine at position 228 and leucine at position 235 in the heavy chain constant region, which are indicated in the EU index as in Kabat et al., are substituted with proline and glutamic acid, respectively.

[3] The antibody according to [1], wherein the antibody has heavy and light chain variable regions of an antibody produced by hybridoma 4D11 (Accession No.: FERM BP-7758), the heavy chain variable region and the light chain variable region are bound to the heavy chain constant region and the human light chain constant region of human IgG4, respectively, such that a heavy chain and a light chain of the antibody are formed, and serine at position 228 and leucine at position 235 in the heavy chain constant region, which are indicated in the EU index as in Kabat et al., are substituted with proline and glutamic acid, respectively.

[4] The antibody according to [1], wherein a variable region shown by the heavy chain amino acid sequence represented by SEQ ID NO: 2 and a variable region shown by the light chain amino acid sequence represented by SEQ ID NO: 4 are bound to the heavy chain constant region of human IgG4 and the human light chain constant region, respectively, such that a heavy chain and a light chain of the antibody are formed, and serine at position 228 and leucine at position 235 in the heavy chain constant region, which are indicated in the EU index as in Kabat et al., are substituted with proline and glutamic acid, respectively.

[5] The antibody according to [1], wherein a heavy chain variable region encoded by a heavy chain nucleic acid sequence represented by SEQ ID NO: 1 and a light chain variable region encoded by a light chain nucleic acid sequence represented by SEQ ID NO: 3 are bound to the heavy chain constant region of human IgG4 and the human light chain constant region, respectively, such that a heavy chain and a light chain of the antibody are formed, and serine at position 228 and leucine at position 235 in the heavy chain constant region, which are indicated in the EU index as in Kabat et al., are substituted with proline and glutamic acid, respectively.

[6] The antibody according to [1], wherein the antibody has the heavy chain shown by the heavy chain amino acid sequence represented by SEQ ID NO: 44, in which serine at position 228, leucine at position 235, and arginine at position 409 in a heavy chain constant region, which are indicated in the EU index as in Kabat et al., are substituted with proline, glutamic acid, and lysine, threonine, methionine, or leucine, respectively, and the light chain shown by the light chain amino acid sequence represented by SEQ ID NO: 46.

[7] The antibody according to [1], wherein the antibody has the heavy chain encoded by a nucleic acid sequence represented by SEQ ID NO: 43, in which serine at position 228, leucine at position 235, and arginine at position 409 in a heavy chain constant region, which are indicated in the EU index as in Kabat et al., are substituted with proline, glutamic acid, and lysine, threonine, methionine, or leucine, respectively, and the light chain encoded by a nucleic acid sequence represented by SEQ ID NO: 45.

[8] The antibody according to [1] or [2], which is an anti-CD40 antibody.

[9] A method for producing an antibody, comprising the step of substituting arginine at position 409 in a heavy chain constant region of human IgG4, which is indicated in the EU index as in Kabat et al., with lysine, threonine, methionine, or leucine.

[10] A method for inhibiting antibody aggregation, wherein arginine at position 409 in a heavy chain constant region of human IgG4, which is indicated in the EU index as in Kabat et al., is substituted with lysine, threonine, methionine, or leucine.

[11] A method for producing an antibody, comprising the steps of:
producing an expression vector having genes encoding the heavy chain and the light chain of the antibody according to any one of [1] to [7];
introducing the expression vector into a host;
culturing the host; and
obtaining the antibody from the culture product.

[12] A method for producing an antibody, comprising the steps of:
producing an expression vector having a variable region of the heavy chain nucleic acid sequence represented by SEQ ID NO: 1 and a variable region of the light chain nucleic acid sequence represented by SEQ ID NO: 3;
introducing the expression vector into a host;
culturing the host; and
obtaining the antibody from the culture product.

[13] A method for producing an antibody, comprising the steps of:
producing an expression vector having a heavy chain nucleic acid sequence represented by SEQ ID NO: 47 and a light chain nucleic acid sequence represented by SEQ ID NO: 45;
introducing the expression vector into a host;
culturing the host; and
obtaining the antibody from the culture product.

[14] A pharmaceutical composition comprising, as an active ingredient, the antibody according to any one of [3] to [7].
[15] A therapeutic agent for transplantation rejection, autoimmune diseases, cancer, arteriosclerosis, nephritis, Alzheimer's disease, or amyloidosis, comprising, as an active ingredient, the antibody according to any one of [3] to [7].

This description includes part or all of the contents as disclosed in the description of Japanese Patent Application No. 2004-275908, which is a priority document of the present application.

EFFECTS OF THE INVENTION

The antibody of the present invention, in which arginine (R) at position 409 of human IgG4 is substituted with lysine (K), threonine (T), methionine (M), or leucine (L), is characterized in that antigen-binding ability is maintained and aggregate formation, particularly aggregate formation at low pH, is inhibited. Thus, it is possible to stably produce the antibody of the present invention as a pharmaceutical agent. Further, when such antibody is administered to a test subject, it becomes possible to easily avoid adverse effects that are induced by incorporation of an antibody aggregate. Thus, it is possible to safely use such antibody.

BEST MODE FOR CARRYING OUT THE INVENTION

Figure 1A:
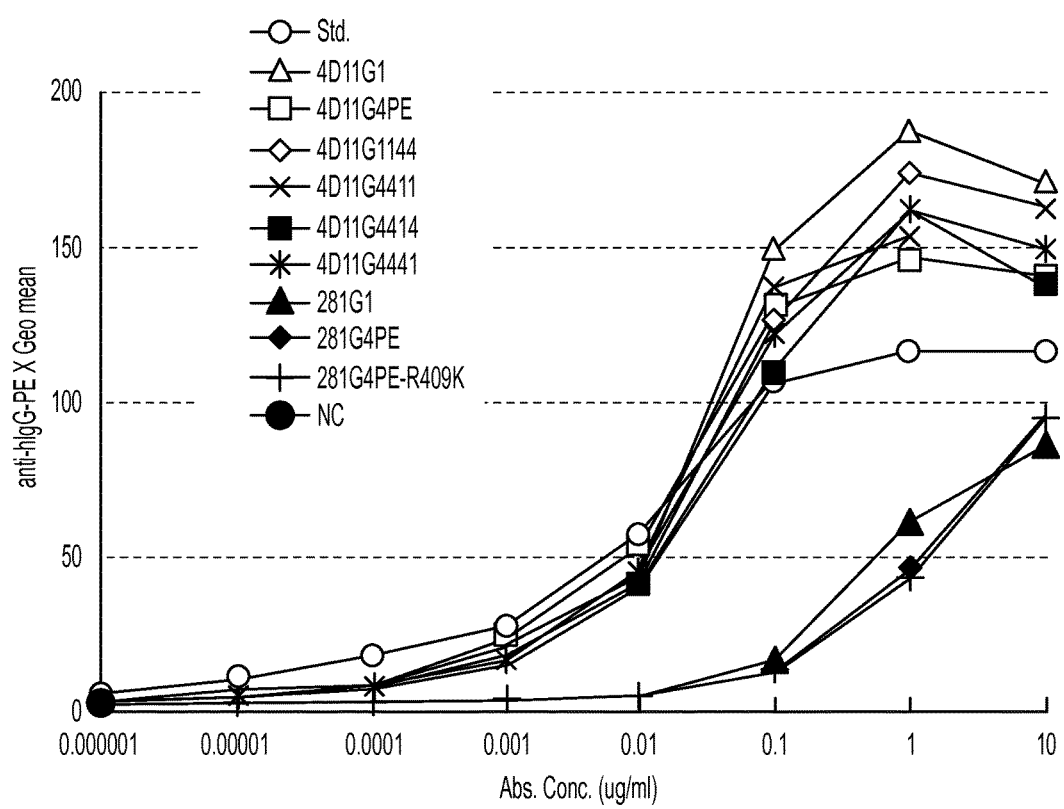
FIG. 1A shows results on the basis of binding activity, indicating that changes in a primary structure of the constant region cause no change in antibody-binding ability.

1. An H chain comprises two regions, which are a variable region involved in determination of antigen-binding specificity and a constant region involved in the expression of effector functions of an antibody. In a variable region, the sequence structure of an antigen-binding site varies as a result of gene recombination that takes place in the region and introduction of somatic cell mutation. Such variation contributes to the obtaining of a property whereby numerous foreign antigens can be recognized.

In addition, antibodies are essentially molecules that function to protect living bodies against cancer and foreign cells of microorganisms and viruses, and thus they have a function of killing and eliminating such cells bound thereto. Such function is referred to as the "effector function." Such lethal function is composed of two different activities, called antibody-dependent cellular cytotoxicity (abbreviated as ADCC hereinafter) and complement-dependent cytotoxicity (abbreviated as CDC hereinafter). ADCC indicates a type of cytotoxicity induced by activation of macrophages, NK cells, neutrophil cells, and the like, which have bound to the constant region of an antibody via FcR that has been expressed on their surface. Meanwhile, CDC indicates a type of cytotoxicity induced by activation of a complement system, which occurs through antibody-antigen binding. These activities are known to vary depending on antibody subclass (Charles A. Janeway et al., Immunology, 1997, Current Biology Ltd./Garland Publishing Inc.).

While antigen-binding specificity is maintained, antibody stability of IgG4 can be improved. Specifically, such improvement can be achieved by substituting arginine (R) at position 409 of IgG4 with glutamic acid (E), phenylalanine (F), isoleucine (I), asparagine (N), glutamine (Q), serine (S), valine (V), tryptophan (W), tyrosine (Y), lysine (K), threonine (T), methionine (M), or leucine (L). Preferably, substitution with lysine (K), threonine (T), methionine (M), or leucine (L) is carried out. Most preferably, substitution with lysine (K) is carried out.

In addition, specifically, such improvement can be achieved by substituting a CH3 domain of IgG4 with a CH3 domain of IgG1 or substituting CH2 and CH3 domains of IgG4 with CH2 and CH3 domains of IgG1.

The term "antibody having improved stability" with reference to the present invention indicates an antibody that is less likely to form an aggregate under acidic, or low-pH, conditions. For instance, upon treatment at pH 3.5 for 10 minutes or 60 minutes, the content of aggregate formed with such antibody is not more than 10%, preferably not more than 5%, and further preferably not more than 1%. The aggregate content can be measured by liquid chromatography or the like.

In addition, the term "antibody having improved physical properties" with reference to the present invention indicates a stabilized antibody in which ADCC and/or CDC are controlled to achieve desired levels and a stabilized antibody in which and FcR-binding ability is controlled to achieve a desired level thereof. Control of ADCC and/or CDC and control of FcR-binding ability can be carried out by introducing a mutation into an antibody in a manner described below.

ADCC and/or CDC can be attenuated or enhanced by introducing further adequate mutations into an antibody having improved stability.

For instance, L235, D265, D270, K322, P331, and P329 are thought to play an important role in terms of the ability to activate a complement of human IgG. (Each alphabetical letter stands for a corresponding amino acid and each number is a number according to the EU index proposed by Kabat et al. (Kabat et al., Sequences of proteins of Immunological Interest, 1991 Fifth edition), and the same applies hereinafter.) By substituting such region with another amino acid, CDC activity can be attenuated (Esohe E. Idusogie et al. J. Immunol. 2000, 164: 4178-4184; Yuanyuan Xu et al. J. Biol. Chem. 1994, 269: 3469-3474; Brekke, O. H. et al. Eur. J. Immunol. 1994, 24: 2542; Morgan, A., et al., Immunology 1995, 86: 319; Lund, J., et al., J. Immunol., 1996, 157: 4963; and Tao, M. H., et al., J. Exp. Med. 1993, 178:

661). Specifically, such attenuation can be carried out by substituting D270, K322, P329, or P331 with A or substituting P331 with S or G.

In addition, Glu233-Ser239, Gly316-Lys338, Lys274-Arg301, Tyr407-Arg416, Asn297, Glu318, Leu234-Ser239, Asp265-Glu269, Asn297-Thr299, and Ala327-Ile332 are thought to be involved in the binding between IgG and FcR (Duncan, A. R., Woof, J. M., Partridge, L. J., Burton, D. R., and Winter, G. (1988) Nature 332, 563-564; Gessner, J. E., Heiken, H., Tamm, A., and Schmidt, R. E. (1998) Ann. Hematol. 76, 231-248; Gavin, A., Hulett, M., and Hogarth, P. M. (1998) in The Immunoglobulin Receptors and Their Physiological and Pathological Roles in Immunity (van de Winkel, J. G. J., and Hogarth, P. M., eds), pp. 11-35; Kluwer Academic Publishers Group, Dordrecht, The Netherlands, Sautes, C. (1997) in Cell-mediated Effects of Immunoglobulins (Fridman, W. H., and Sautes, C., eds), pp. 29-66; R. G. Landes Co., Austin, Tex., Da'ron, M. (1997) Annu. Rev. Immunol. 15, 203-234; Canfield, S. M., and Morrison, S. L. (1991) J. Exp. Med. 173, 1483-1491; Chappel, M. S., Isenman, D. E., Everett, M., Xu, Y.-Y., Dorrington, K. J., and Klein, M. H. (1991) Proc. Natl. Acad. Sci. U.S.A. 88, 9036-9040; Woof, J. M., Partridge, L. J., Jefferis, R., and Burton, D. R. (1986) Mol. Immunol. 23, 319-330; and Wines, B. D., Powell, M. S., Parren, P. W. H. I., Barnes, N., and Hogarth, P. M. (2000) J. Immunol. 164, 5313-5318). By introducing mutation into such regions, ADCC activity can be reduced. Specifically, FcR-binding ability can be reduced by substituting L235 and G237 with E and A, respectively.

In addition, ADCC and/or CDC of an antibody having improved stability can be enhanced by introducing the mutation described above in a reversed manner. Specifically, by converting S at position 331 of IgG4 to P, CDC activity can be enhanced (Yuanyuan Xu et al. J Biol. Chem. 1994. 269. 3469-3474).

An antibody having improved stability in which arginine (R) at position 409 of IgG4 is substituted with lysine (K), threonine (T), methionine (M), or leucine (L) is not particularly limited. However, examples thereof include anti-CD40 antibodies. More specifically, examples thereof include 4D11, KM281-1-10, and F4-465 described in WO03/88186.

In addition, the mutation of R409 of IgG4 into K at a frequency of 1/45 in humans has been reported; however, such mutation and the stability of such IgG4 are not described in the report (Molecular characterization of immunoglobulin G4 isoallotype A. Brusco, S. Saviozzi, F. Clinque, M. DeMarchi, C. Boccazzi, G. de Lange, A. M. van Leeuwen, A. O. Carbonara European J Immunogenetics, 1998, 25, 349-355).

2. Definition

The terms used herein are defined as follows.

The term "CD40" used herein indicates a polypeptide having the amino acid sequence described in E. A. Clark et al., Proc. Natl. Acad. Sci. U.S.A. 83: 4494, 1986, or I. Stamenkovic et al., EMBO J. 8: 1403, 1989, and particularly, an antigenic polypeptide expressed on the surfaces of B cells, DC, macrophages, endothelial cells, epithelial cells, or tumor cells derived from such cells.

The term "anti-CD40 antibody" used herein indicates any monoclonal or polyclonal antibody to a cell-expressed CD40, a full-length CD40, or a partial-length CD40. Preferably, such antibody is a monoclonal antibody.

The term "antibody" of the invention indicates antibodies that are derived from genes (collectively referred to as antibody genes) encoding a heavy chain variable region, a heavy chain constant region, a light chain variable region, and a light chain constant region, which together constitute an immunoglobulin. The antibody of the present invention includes an antibody of any immunoglobulin class and an antibody having any isotype.

The terms "CH1 domain," "hinge region," "CH2 domain," and "CH3 domain" used herein each indicate a portion of the heavy-chain constant region of an antibody, and they are based on the EU index as in Kabat et al. (Kabat et al., Sequences of proteins of immunological interest, 1991 Fifth edition). By definition, the CH1 domain ranges from 118 to 215 according to the EU index, the hinge region ranges from 216 to 237 according to the EU index, the CH2 domain ranges from 238 to 340 according to the EU index, and the CH3 domain ranges from 341 to 446 according to the EU index.

The term "human antibody" with reference to the present invention indicates an antibody which is an expression product of a human-derived antibody gene. The light chain of a human antibody comprises either κ or λ. The heavy chain of a human antibody comprises the 5 different classes of IgG, IgA, IgM, IgD, and IgE. Further, IgG comprises the 4 subclasses of IgG1, IgG2, IgG3, and IgG4.

The term "antibody mutant" used herein indicates a mutant derived from an antibody that is produced by a hybridoma, such antibody having an amino acid sequence subjected to deletion, substitution, insertion, or addition of at least one amino acid. The antibody mutant of the present invention can be adequately produced with the use of the following methods or the like that are known to persons skilled in the art: a method for isolating an antibody gene from a hybridoma; sequence information of the human antibody constant region; and a method of site-directed mutagenesis in genes.

The antibody of the present invention includes an antibody subjected to deletion, substitution, insertion, or addition of "several" amino acid. In such case, the phrase "several" indicates specifically 1 to 10, preferably 1 to 8, further preferably 1 to 5, and most preferably 1 or 2. In addition, the aforementioned deletion, substitution, insertion, or addition preferably occurs in a heavy chain constant region of an antibody. Specific examples of such antibody include: (1) an antibody in which serine at position 228 in a heavy chain constant region of human IgG4, which is indicated in the EU index as in Kabat et al., is substituted with proline; (2) an antibody in which leucine at position 235 in a heavy chain constant region of human IgG4, which is indicated in the EU index as in Kabat et al., is substituted with glutamic acid; and (3) an antibody in which serine at position 228 and leucine at position 235 in a heavy chain constant region of human IgG4, which are indicated in the EU index as in Kabat et al., are substituted with proline and glutamic acid, respectively.

In addition, the antibody of the present invention includes a chimeric antibody and a humanized antibody. Such chimeric antibody comprises portions of antibodies derived from two or more species (e.g., a variable region of murine antibody and a constant region of human antibody) (e.g., EP Patent Applications nos. 120694 and 125023). A humanized antibody is produced from murine CDR, a human variable region framework, and a human constant region with the use of CDR grafting techniques or the like (e.g., Riechmann, et al., Nature (1988), 332, 323-327).

The antibody of the present invention can be obtained by incorporating the antibody gene into an expression vector, introducing the vector into a suitable host cell, harvesting the antibody from the cultured cells or the supernatant, and purifying the same.

Such vector used may be a phage or a plasmid that can autonomously replicate in the host cell or can be integrated into the chromosomes of the host cell. Such plasmid DNA may be derived from *Escherichia coli*, *Bacillus subtilis*, or a yeast. Such phage DNA may be a λ phage or the like.

The host cell used for transformation is not particularly limited as long as it can express the target gene. Examples of such host cell include bacteria (e.g., *Escherichia coli* and *Bacillus subtilis*), yeasts, animal cells (e.g., COS cell and CHO cell) and insect cells.

Any known methods for introducing a gene into a host may be used (e.g., a calcium ion method, electroporation, a spheroplast method, a lithium acetate method, a calcium phosphate method, and lipofection). Examples of a method for introducing a gene into an animal described below include microinjection, a method for introducing a gene into an ES cell using electroporation or lipofection, and nuclear transplantation.

The term "culture product" of the present invention indicates (a) culture supernatant, (b) cultured cells, cultured bacterial cells, or disrupted cells, or (c) secretion of a transformant. In order to culture a transformant, static culture, roller bottle culture, or the like may be employed with the use of a medium suitable for the host used.

After culture, if an antibody protein of interest is produced in bacterial cells or other cells, the antibody is harvested by disrupting the bacterial cells or cells. If the antibody of interest is produced in the external environment of the bacterial cells or cells, the culture solution is used as is or after being separated from the bacterial cells or cells by centrifugation or other means. Thereafter, a biochemical process with any form of chromatography used for isolation/purification of proteins is employed alone or optionally in combination such that the antibody of interest can be isolated and purified from the culture product.

Furthermore, a host animal having an endogenous gene into which the gene of an antibody of interest has been incorporated, such as, for example, a transgenic bovine, a transgenic goat, a transgenic sheep, or a transgenic pig, may be produced by a technique for creating a transgenic animal. In such case, it is then possible to mass-produce a monoclonal antibody derived from the antibody gene with the use of milk that has been secreted from such transgenic animal (Wright, G., et al., (1991) Bio/Technology 9, 830-834). It is possible to carry out in vitro culture of a hybridoma by allowing a hybridoma to proliferate, maintaining and preserving the hybridoma, and applying a known nutrient medium used for monoclonal antibody production or any nutrient medium that is derived and prepared from a known basic medium to the culture supernatant based on properties of a cell species to be cultured, experimental and study purposes, and various conditions for culture and the like.

3. Pharmaceutical Composition

A pharmaceutical composition containing a formulation of the purified antibody of the present invention is also within the scope of the present invention. Such pharmaceutical composition preferably contains a physiologically acceptable diluent or carrier in addition to the antibody, and may be in the form of a mixture with a different antibody or a different drug such as an antibiotic agent. Examples of a suitable carrier include, but are not limited to, physiological saline, phosphate buffered physiological saline, a phosphate buffered physiological saline glucose solution, and buffered physiological saline. Alternatively, the antibody may be freeze-dried and it may be reconstituted when necessary with the addition of a buffered aqueous solution as described above before use. The pharmaceutical composition may be administered via the oral route or the parenteral route such as via intravenous, intramuscular, subcutaneous or intraperitoneal injection or dosing.

In the above case, a single effective dose, which is a combination of the antibody of the present invention with a suitable diluent and a physiologically acceptable carrier, is from 0.0001 mg to 100 mg per kg of body weight administered from once every two days to once every 8 weeks.

The anti-CD40 antibody of the present invention can be used for therapies for transplantation rejection (induced after kidney transplantation, heart transplantation, liver transplantation, pancreas transplantation, intestine transplantation, xenograft, and the like), autoimmune diseases (e.g., inflammatory intestinal diseases (e.g., clone disease and ulcerative colitis), systemic lupus erythematosus (SLE), idiopathic thrombocytopenic purpura (ITP), multiple sclerosis, psoriasis, and rheumatism), cancer (e.g., lung cancer, large intestine cancer, colon cancer, rectal cancer, pancreatic cancer, liver cancer, prostate cancer, urinary bladder cancer, breast cancer, and gastric cancer), arteriosclerosis, nephritis, Alzheimer's disease, and amyloidosis.

EXAMPLE

The present invention is hereafter described in greater detail with reference to the following examples, although the technical scope of the present invention is not limited thereto.

Example 1: Production of Anti-CD40 Antibodies and IgG1/IgG4 Constant Region Fusion Products Antibodies were produced with the use of heavy and light chain variable regions of 4D11, KM281-1-10, and F4-465, which are anti-CD40 antibodies described in WO02/088186. These 3 antibodies are known to act as antagonists. 4D11, KM281-1-10, and F4-465 are antibodies produced by hybridomas 4D11, KM281-1-10, and F4-465, respectively. Hybridomas 4D11 and KM281-1-10 have been deposited with the International Patent Organism Depositary, National Institute of Advanced Industrial Science and Technology, at AIST (Tsukuba Central 6, 1-1-1 Higashi, Tsukuba, Ibaraki, Japan) under Accession Nos. FERM BP-7758 and FERM BP-7579 as of Sep. 27, 2001, and May 9, 2001, respectively. In addition, F4-465 has been deposited with the American Type Culture Collection (ATCC), (10801 University Boulevard, Manassas, Va. 20110-2209, U.S.A.) under accession no. ATCC PTA-3338 as of Apr. 24, 2001.

DNAs encoding the heavy and light chain variable regions of 4D11 and the amino acid sequences of the heavy and light chains of 4D11 will be presented below.

The translation initiation site of the heavy chain nucleic acid sequence is an ATG codon starting from adenine (A) at position 16 from the 5' end of SEQ ID NO: 1.

In the heavy chain nucleic acid sequence (SEQ ID NO: 1) of 4D11, the boundary between the signal sequence and the variable region was predicted to be located between cytosine (C) at position 93 and cytosine (C) at position 94, and the boundary between the variable region and the constant region was predicted to be located between adenine (A) at position 456 and guanine (G) at position 457 (with the use of gene sequence prediction software (Signal P ver.2)).

In the heavy chain amino acid sequence (SEQ ID NO: 2) of 4D11, the boundary between the signal sequence and the variable region was predicted to be located between serine (S) at position 26 and glutamine (Q) at position 27, and the boundary between the variable region and the constant region was predicted to be located between serine (S) at position 147 and alanine (A) at position 148.

Accordingly, the heavy chain variable region of 4D11 has a nucleic acid sequence ranging from cytosine (C) at position 94 to adenine (A) at position 456 in SEQ ID NO: 1. In addition, the heavy chain variable region of 4D11 has an amino acid sequence ranging from glutamine (Q) at position 27 to serine (S) at position 147 in SEQ ID NO: 2.

The translation initiation site of the light chain nucleic acid sequence is an ATG codon starting from adenine (A) at position 59 from the 5' end of SEQ ID NO: 3.

In the light chain nucleic acid sequence (SEQ ID NO: 3) of 4D11, the boundary between the signal sequence and the variable region was predicted to be located between thymine (T) at position 124 and guanine (G) at position 125, and the boundary between the variable region and the constant region was predicted to be located between adenine (A) at position 442 and cytosine (C) at position 443 (with the use of gene sequence prediction software (Signal P ver.2)).

In the light chain amino acid sequence (SEQ ID NO: 4) of 4D11, the boundary between the signal sequence and the variable region was predicted to be located between cysteine (C) at position 22 and alanine (A) at position 23, and the boundary between the variable region and the constant region was predicted to be located between lysine (K) at position 128 and arginine (R) at position 129.

Accordingly, the light chain variable region of 4D11 has a nucleic acid sequence ranging from guanine (G) at position 125 to adenine (A) at position 442 of SEQ ID NO: 3. In addition, the light chain variable region of 4D11 has an amino acid sequence ranging from alanine (A) at position 23 to lysine (K) at position 128 of SEQ ID NO: 4. The heavy chain nucleic acid sequence of (SEQ ID NO: 1) of 4D11

ATATGTCGACGAGTCATGGATCTCATGTGCAAGAAAATGAAGCACCTG

TGGTTCTTCCTCCTGCTGGTGGCGGCTCCCAGATGGGTCCTGTCCCAG

CTGCAGCTGCAGGAGTCGGGCCCAGGACTACTGAAGCCTTCGGAGACC

CTGTCCCTCACCTGCACTGTCTCTGGCGGCTCCATCAGCAGTCCTGGT

TACTACGGGGCTGGATCCGCCAGCCCCCAGGGAAGGGGCTGGAGTGG

ATTGGGAGTATCTATAAAAGTGGGAGCACCTACCACAACCCGTCCCTC

AAGAGTCGAGTCACCATATCCGTAGACACGTCCAAGAACCAGTTCTCC

CTGAAGCTGAGCTCTGTGACCGCCGCAGACACGGCTGTGTATTACTGT

ACGAGACCTGTAGTACGATATTTTGGGTGGTTCGACCCCTGGGGCCAG

GGAACCCTGGTCACCGTCTCCTCAGCTAGC

The heavy chain amino acid sequence (SEQ ID NO: 2) of 4D11

MDLMCKKMKHLWFFLLLVAAPRWVLSQLQLQESGPGLLKPSETLSLTC

TVSGGSISSPGYYGGWIRQPPGKGLEWIGSIYKSGSTYHNPSLKSRVT

ISVDTSKNQFSLKLSSVTAADTAVYYCTRPVVRYFGWFDPWGQGTLVT

VSSAS

The light chain nucleic acid sequence (SEQ ID NO: 3) of 4D11

AGATCTTAAGCAAGTGTAACAACTCAGAGTACGCGGGGAGACCCACTC

AGGACACAGCATGGACATGAGGGTCCCCGCTCAGCTCCTGGGGCTTCT

GCTGCTCTGGCTCCCAGGTGCCAGATGTGCCATCCAGTTGACCCAGTC

TCCATCCTCCCTGTCTGCATCTGTAGGAGACAGAGTCACCATCACTTG

CCGGGCAAGTCAGGGCATTAGCAGTGCTTTAGCCTGGTATCAGCAGAA

ACCAGGGAAAGCTCCTAAGCTCCTGATCTATGATGCCTCCAATTTGGA

AAGTGGGGTCCCATCAAGGTTCAGCGGCAGTGGATCTGGGACAGATTT

CACTCTCACCATCAGCAGCCTGCAGCCTGAAGATTTTGCAACTTATTA

CTGTCAACAGTTTAATAGTTACCCGACGTTCGGCCAAGGGACCAAGGT

GGAAATCAAACGTACG

The light chain amino acid sequence (SEQ ID NO: 4) of 4D11

MDMRVPAQLLGLLLLWLPGARCAIQLTQSPSSLSASVGDRVTITCRAS

QGISSALAWYQQKPGKAPKLLIYDASNLESGVPSRFSGSGSGTDFTLT

ISSLQPEDFATYYCQQFNSYPTFGQGTKVEIKRT

The heavy and light chain nucleic acid sequences of an antibody (hereafter to be referred to as 4D11G4) created by substituting the heavy chain constant region of 4D11 with IgG4 will be presented below.
The heavy chain nucleic acid sequence (SEQ ID NO: 43) of 4D11G4

ATGGATCTCATGTGCAAGAAAATGAAGCACCTGTGGTTCTTCCTCCTGCT

GGTGGCGGCTCCCAGATGGGTCCTGTCCCAGCTGCAGCTGCAGGAGTCGG

GCCCAGGACTACTGAAGCCTTCGGAGACCCTGTCCCTCACCTGCACTGTC

TCTGGCGGCTCCATCAGCAGTCCTGGTTACTACGGGGGCTGGATCCGCCA

GCCCCCAGGGAAGGGGCTGGAGTGGATTGGGAGTATCTATAAAAGTGGGA

GCACCTACCACAACCCGTCCCTCAAGAGTCGAGTCACCATATCCGTAGAC

ACGTCCAAGAACCAGTTCTCCCTGAAGCTGAGCTCTGTGACCGCCGCAGA

CACGGCTGTGTATTACTGTACGAGACCTGTAGTACGATATTTTGGGTGGT

TCGACCCCTGGGGCCAGGGAACCCTGGTCACCGTCTCCTCAGCTAGCACC

AAGGGGCCATCCGTCTTCCCCCTGGCGCCCTGCTCCAGGAGCACCTCCGA

GAGCACAGCCGCCCTGGGCTGCCTGGTCAAGGACTACTTCCCCGAACCGG

TGACGGTGTCGTGGAACTCAGGCGCCCTGACCAGCGGCGTGCACACCTTC

CCGGCTGTCCTACAGTCCTCAGGACTCTACTCCCTCAGCAGCGTGGTGAC

CGTGCCCTCCAGCAGCTTGGGCACGAAGACCTACACCTGCAACGTAGATC

ACAAGCCCAGCAACACCAAGGTGGACAAGAGAGTTGAGTCCAAATATGGT

CCCCCATGCCCATCATGCCCAGCACCTGAGTTCCTGGGGGGACCATCAGT

CTTCCTGTTCCCCCCAAAACCCAAGGACACTCTCATGATCTCCCGGACCC

CTGAGGTCACGTGCGTGGTGGTGGACGTGAGCCAGGAAGACCCCGAGGTC

CAGTTCAACTGGTACGTGGATGGCGTGGAGGTGCATAATGCCAAGACAAA

-continued

GCCGCGGGAGGAGCAGTTCAACAGCACGTACCGTGTGGTCAGCGTCCTCA

CCGTCCTGCACCAGGACTGGCTGAACGGCAAGGAGTACAAGTGCAAGGTC

TCCAACAAAGGCCTCCCGTCCTCCATCGAGAAAACCATCTCCAAAGCCAA

AGGGCAGCCCCGAGAGCCACAGGTGTACACCCTGCCCCCATCCCAGGAGG

AGATGACCAAGAACCAGGTCAGCCTGACCTGCCTGGTCAAAGGCTTCTAC

CCCAGCGACATCGCCGTGGAGTGGGAGAGCAATGGGCAGCCGGAGAACAA

CTACAAGACCACGCCTCCCGTGCTGGACTCCGACGGCTCCTTCTTCCTCT

ACAGCAGGCTAACCGTGGACAAGAGCAGGTGGCAGGAGGGGAATGTCTTC

TCATGCTCCGTGATGCATGAGGCTCTGCACAACCACTACACACAGAAGAG

CCTCTCCCTGTCTCTGGGTAAATGA

The heavy chain amino sequence (SEQ ID NO: 44) of 4D11G4

MDLMCKKMKHLWFFLLLVAAPRWVLSQLQLQESGPGLLKPSETLSLTCTV

SGGSISSPGYYGGWIRQPPGKGLEWIGSIYKSGSTYHNPSLKSRVTISVD

TSKNQFSLKLSSVTAADTAVYYCTRPVVRYFGWFDPWGQGTLVTVSSAST

KGPSVFPLAPCSRSTSESTAALGCLVKDYFPEPVTVSWNSGALTSGVHTF

PAVLQSSGLYSLSSVVTVPSSSLGTKTYTCNVDHKPSNTKVDKRVESKYG

PPCPSCPAPEFLGGPSVFLFPPKPKDTLMISRTPEVTCVVVDVSQEDPEV

QFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFY

PSDIAVEWESNGQPENNYKTTPPVLDSDGSFFLYSRLTVDKSRWQEGNVF

SCSVMHEALHNHYTQKSLSLSLGK

The light chain nucleic acid sequence (SEQ ID NO: 45) of 4D11G4

ATGGACATGAGGGTCCCCGCTCAGCTCCTGGGGCTTCTGCTGCTCTGGCT

CCCAGGTGCCAGATGTGCCATCCAGTTGACCCAGTCTCCATCCTCCCTGT

CTGCATCTGTAGGAGACAGAGTCACCATCACTTGCCGGGCAAGTCAGGGC

ATTAGCAGTGCTTTAGCCTGGTATCAGCAGAAACCAGGGAAAGCTCCTAA

GCTCCTGATCTATGATGCCTCCAATTTGGAAAGTGGGGTCCCATCAAGGT

TCAGCGGCAGTGGATCTGGGACAGATTTCACTCTCACCATCAGCAGCCTG

CAGCCTGAAGATTTTGCAACTTATTACTGTCAACAGTTTAATAGTTACCC

GACGTTCGGCCAAGGGACCAAGGTGGAAATCAAACGTACGGTGGCTGCAC

CATCTGTCTTCATCTTCCCGCCATCTGATGAGCAGTTGAAATCTGGAACT

GCCTCTGTTGTGTGCCTGCTGAATAACTTCTATCCCAGAGAGGCCAAAGT

ACAGTGGAAGGTGGATAACGCCCTCCAATCGGGTAACTCCCAGGAGAGTG

TCACAGAGCAGGACAGCAAGGACAGCACCTACAGCCTCAGCAGCACCCTG

ACGCTGAGCAAAGCAGACTACGAGAAACACAAAGTCTACGCCTGCGAAGT

CACCCATCAGGGCCTGAGCTCGCCCGTCACAAAGAGCTTCAACAGGGGAG

AGTGTTGA

The light chain amino sequence (SEQ ID NO: 46) of 4D11G4

MDMRVPAQLLGLLLLWLPGARCAIQLTQSPSSLSASVGDRVTITCRASQG

ISSALAWYQQKPGKAPKLLIYDASNLESGVPSRFSGSGSGTDFTLTISSL

QPEDFATYYCQQFNSYPTFGQGTKVEIKRTVAAPSVFIFPPSDEQLKSGT

ASVVCLLNNFYPREAKVQWKVDNALQSGNSQESVTEQDSKDSTYSLSSTL

TLSKADYEKHKVYACEVTHQGLSSPVTKSFNRGEC

The heavy chain nucleic acid sequence of 4D11 created by substituting the heavy chain constant region, serine at position 228, leucine at position 235, and arginine at position 409 with IgG4, proline, glutamic acid, and lysine, respectively, will be presented below (such sequence being hereafter referred to as 4D11G4PEK).

The heavy chain nucleic acid sequence (SEQ ID NO: 47) of 4D11G4PEK

ATGGATCTCATGTGCAAGAAAATGAAGCACCTGTGGTTCTTCCTCCTGCT

GGTGGCGGCTCCCAGATGGGTCCTGTCCCAGCTGCAGCTGCAGGAGTCGG

GCCCAGGACTACTGAAGCCTTCGGAGACCCTGTCCCTCACCTGCACTGTC

TCTGGCGGCTCCATCAGCAGTCCTGGTTACTACGGGGGCTGGATCCGCCA

GCCCCCAGGGAAGGGGCTGGAGTGGATTGGGAGTATCTATAAAAGTGGGA

GCACCTACCACAACCCGTCCCTCAAGAGTCGAGTCACCATATCCGTAGAC

ACGTCCAAGAACCAGTTCTCCCTGAAGCTGAGCTCTGTGACCGCCGCAGA

CACGGCTGTGTATTACTGTACGAGACCTGTAGTACGATATTTTGGGTGGT

TCGACCCCTGGGGCCAGGGAACCCTGGTCACCGTCTCCTCAGCTAGCACC

AAGGGGCCATCCGTCTTCCCCCTGGCGCCCTGCTCCAGGAGCACCTCCGA

GAGCACAGCCGCCCTGGGCTGCCTGGTCAAGGACTACTTCCCCGAACCGG

TGACGGTGTCGTGGAACTCAGGCGCCCTGACCAGCGGCGTGCACACCTTC

CCGGCTGTCCTACAGTCCTCAGGACTCTACTCCCTCAGCAGCGTGGTGAC

CGTGCCCTCCAGCAGCTTGGGCACGAAGACCTACACCTGCAACGTAGATC

ACAAGCCCAGCAACACCAAGGTGGACAAGAGAGTTGAGTCCAAATATGGT

CCCCCATGCCCACCATGCCCAGCACCTGAGTTCGAGGGGGGACCATCAGT

CTTCCTGTTCCCCCCAAAACCCAAGGACACTCTCATGATCTCCCGGACCC

CTGAGGTCACGTGCGTGGTGGTGGACGTGAGCCAGGAAGACCCCGAGGTC

CAGTTCAACTGGTACGTGGATGGCGTGGAGGTGCATAATGCCAAGACAAA

GCCGCGGGAGGAGCAGTTCAACAGCACGTACCGTGTGGTCAGCGTCCTCA

CCGTCCTGCACCAGGACTGGCTGAACGGCAAGGAGTACAAGTGCAAGGTC

TCCAACAAAGGCCTCCCGTCCTCCATCGAGAAAACCATCTCCAAAGCCAA

AGGGCAGCCCCGAGAGCCACAGGTGTACACCCTGCCCCCATCCCAGGAGG

AGATGACCAAGAACCAGGTCAGCCTGACCTGCCTGGTCAAAGGCTTCTAC

CCCAGCGACATCGCCGTGGAGTGGGAGAGCAATGGGCAGCCGGAGAACAA

CTACAAGACCACGCCTCCCGTGCTGGACTCCGACGGCTCCTTCTTCCTCT

ACAGCAAGCTAACCGTGGACAAGAGCAGGTGGCAGGAGGGGAATGTCTTC

-continued

TCATGCTCCGTGATGCATGAGGCTCTGCACAACCACTACACACAGAAGAG

CCTCTCCCTGTCTCTGGGTAAATGA

The heavy chain amino sequence (SEQ ID NO: 48) of 4D11G4PEK

MDLMCKKMKHLWFFLLLVAAPRWVLSQLQLQESGPGLLKPSETLSLTCTV

SGGSISSPGYYGGWIRQPPGKGLEWIGSIYKSGSTYHNPSLKSRVTISVD

TSKNQFSLKLSSVTAADTAVYYCTRPVVRYFGWFDPWGQGTLVTVSSAST

KGPSVFPLAPCSRSTSESTAALGCLVKDYFPEPVTVSWNSGALTSGVHTF

PAVLQSSGLYSLSSVVTVPSSSLGTKTYTCNVDHKPSNTKVDKRVESKYG

PPCPPCPAPEFEGGPSVFLFPPKPKDTLMISRTPEVTCVVVDVSQEDPEV

QFNWYVDGVEVHNAKTKPREEQFNSTYRVVSVLTVLHQDWLNGKEYKCKV

SNKGLPSSIEKTISKAKGQPREPQVYTLPPSQEEMTKNQVSLTCLVKGFY

PSDIAVEWESNGQPENNYKTTPPVLDSDGSFFLYSKLTVDKSRWQEGNVF

SCSVMHEALHNHYTQKSLSLSLGK

DNAs encoding the heavy and light chain variable regions of KM281-1-10 and the amino acid sequences of the heavy and light chains of KM281-1-10 will be presented below. The translation initiation site of the heavy chain nucleic acid sequence is an ATG codon starting from adenine (A) at position 52 from the 5' end of SEQ ID NO: 5. In the heavy chain nucleic acid sequence (SEQ ID NO: 5) of KM281-1-10, the boundary between the signal sequence and the variable region was predicted to be located between cytosine (C) at position 108 and cytosine (C) at position 109, and the boundary between the variable region and the constant region was predicted to be located between adenine (A) at position 468 and guanine (G) at position 469 (with the use of gene sequence prediction software (Signal P ver.2)).

In the heavy chain amino acid sequence (SEQ ID NO: 6) of KM281-1-10, the boundary between the signal sequence and the variable region was predicted to be located between serine (S) at position 19 and glutamine (Q) at position 20, and the boundary between the variable region and the constant region was predicted to be located between serine (S) at position 139 and alanine (A) at position 140.

Accordingly, the heavy chain variable region (mature portion) of KM281-1-10 has a nucleic acid sequence ranging from cytosine (C) at position 109 to adenine (A) at position 468 in SEQ ID NO: 5. In addition, the heavy chain variable region (mature portion) of KM281-1-10 has an amino acid sequence ranging from glutamine (Q) at position 20 to serine (S) at position 139 in SEQ ID NO: 6.

The translation initiation site of the light chain nucleic acid sequence is an ATG codon starting from adenine (A) at position 41 from the 5' end of SEQ ID NO: 7.

In the light chain nucleic acid sequence (SEQ ID NO: 7) of KM281-1-10, the boundary between the signal sequence and the variable region was predicted to be located between adenine (A) at position 100 and guanine (G) at position 101, and the boundary between the variable region and the constant region was predicted to be located between adenine (A) at position 424 and cytosine (C) at position 425 (with the use of gene sequence prediction software (Signal P ver.2)).

In the light chain amino acid sequence (SEQ ID NO: 8) of KM281-1-10, the boundary between the signal sequence and the variable region was predicted to be located between glycine (G) at position 20 and glutamic acid (E) at position 21, and the boundary between the variable region and the constant region was predicted to be located between lysine (K) at position 128 and arginine (R) at position 129.

Accordingly, the light chain variable region (mature portion) of KM281-1-10 has a nucleic acid sequence ranging from guanine (G) at position 101 to adenine (A) at position 424 of SEQ ID NO: 7. In addition, the light chain variable region (mature portion) of KM281-1-10 has an amino acid sequence ranging from glutamic acid (E) at position 21 to lysine (K) at position 128 of SEQ ID NO: 8.

The present invention relates to an antibody having the aforementioned mature portion. The present invention encompasses an antibody stabilized through the aforementioned mutation.

The heavy chain nucleic acid sequence (SEQ ID NO: 5) of KM281-1-10

CTGAACACAGACCCGTCGACTTTGAGAGTCCTGGACCTCCTGTGCAAGAA

CATGAAACATCTGTGGTTCTTCCTTCTCCTGGTGGCAGCTCCCAGATGGG

TCCTGTCCCAGGTGCAGCTGCAGGAGTCGGGCCCAGGACTGGTGAAGCCT

TCGGAGACCCTGTCCCTCACCTGCACTGTCTCTGGTGGCTCCATCAGTGG

TTACTACTGGAGCTGGATCCGGCAGCCCCCAGGGAAGGGACTGGAGTGGA

TTGGGTATATCTATTACAGTGGGAGCACCAACTACAATCCCTCCCTCAAG

AGTCGAGTCACCATATCAGTAGACACGTCCAAGAACCAGTTCTCCCTGAA

GCTGAATTCTGTGACCGCTGCGGACACGGCCGTGTATTACTGTGCGAGAG

CCCCCTTGCACGGTGACTACAAATGGTTCCACCCCTGGGGCCAGGGAACC

CTGGTCACCGTCTCCTCAGCTAGCACCAAGG

The heavy chain amino acid sequence (SEQ ID NO: 6) of KM281-1-10

MKHLWFFLLLVAAPRWVLSQVQLQESGPGLVKPSETLSLTCTVSGGSISG

YYWSWIRQPPGKGLEWIGYIYYSGSTNYNPSLKSRVTISVDTSKNQFSLK

LNSVTAADTAVYYCARAPLHGDYKWFHPWGQGTLVTVSSASTK

The light chain nucleic acid sequence (SEQ ID NO: 7) of KM281-1-10

TCACAGATCTGAGCTGCTCAGTTAGGACCCAGAGGGAACCATGGAAACCC

CAGCGCAGCTTCTCTTCCTCCTGCTACTCTGGCTCCCAGATACCACCGGA

GAAATTGTGTTGACGCAGTCTCCAGGCACCCTGTCTTTGTCTCCAGGGGA

AAGAGCCACCCTCTCCTGCAGGGCCAGTCAGAGTGTTAGCAGCAGCTACT

TAGCCTGGTACCAGCAGAAACCTGGCCAGGCTCCCAGGCTCCTCATCTAT

GGTGCATCCAGCAGGGCCACTGGCATCCCAGACAGGTTCAGTGGCAGTGG

GTCTGGGACAGACTTCACTCTCACCATCAGCAGACTGGAGCCTGAAGATT

TTGCAGTGTATTACTGTCAGCAGTATGGTAGCTCACCGATCACCTTCGGC

CAAGGGACACGACTGGAGATCAAACGTACG

The light chain amino acid sequence (SEQ ID NO: 8) of KM281-1-10

METPAQLLFLLLLWLPDTTGEIVLTQSPGTLSLSPGERATLSCRASQSVS

SSYLAWYQQKPGQAPRLLIYGASSRATGIPDRFSGSGSGTDFTLTISRLE

PEDFAVYYCQQYGSSPITFGQGTRLEIKRT

DNAs encoding the heavy and light chain variable regions of F4-465 and the amino acid sequences of the heavy and light chains of F4-465 will be presented below, respectively.

The translation initiation site of the heavy chain nucleic acid sequence is an ATG codon starting from adenine (A) at position 47 from the 5' end of SEQ ID NO: 9.

In the heavy chain nucleic acid sequence (SEQ ID NO: 9) of F4-465, the boundary between the signal sequence and the variable region was predicted to be located between cytosine (C) at position 103 and cytosine (C) at position 104, and the boundary between the variable region and the constant region was predicted to be located between adenine (A) at position 484 and guanine (G) at position 485 (with the use of gene sequence prediction software (Signal P ver.2)).

In the heavy chain amino acid sequence (SEQ ID NO: 10) of F4-465, the boundary between the signal sequence and the variable region was predicted to be located between serine (S) at position 19 and glutamine (Q) at position 20, and the boundary between the variable region and the constant region was predicted to be located between serine (S) at position 146 and alanine (A) at position 147.

Accordingly, the heavy chain variable region of F4-465 has a nucleic acid sequence ranging from cytosine (C) at position 104 to adenine (A) at position 484 in SEQ ID NO: 9. In addition, the heavy chain variable region of F4-465 has an amino acid sequence ranging from glutamine (Q) at position 20 to serine (S) at position 146 in SEQ ID NO: 10.

The translation initiation site of the light chain nucleic acid sequence is an ATG codon starting from adenine (A) at position 81 from the 5' end of SEQ ID NO: 11.

In the light chain nucleic acid sequence (SEQ ID NO: 11) of F4-465, the boundary between the signal sequence and the variable region was predicted to be located between cytosine (C) at position 137 and thymine (T) at position 138, and the boundary between the variable region and the constant region was predicted to be located between thymine (T) at position 458 and cytosine (C) at position 459 (with the use of gene sequence prediction software (Signal P ver.2)).

In the light chain amino acid sequence (SEQ ID NO: 12) of F4-465, the boundary between the signal sequence and the variable region was predicted to be located between alanine (A) at position 19 and serine (S) at position 20, and the boundary between the variable region and the constant region was predicted to be located between glycine (G) at position 126 and glutamine (Q) at position 127.

Accordingly, the light chain variable region of F4-465 has a nucleic acid sequence ranging from thymine (T) at position 138 to thymine (T) at position 458 of SEQ ID NO: 11. In addition, the light chain variable region of F4-465 has an amino acid sequence ranging from serine (S) at position 20 to glycine (G) at position 126 of SEQ ID NO: 12.

The heavy chain nucleic acid sequence (SEQ ID NO: 9) of F4-465

CTGAACACAGACCCGTCGACTACGCGGGAGACCACAGCTCCACACCATGG

ACTGGACCTGGAGGATCCTATTCTTGGTGGCAGCAGCAACAGGTGCCCAC

TCCCAGGTGCAGCTGGTGCAATCTGGGTCTGAGTTGAAGAAGCCTGGGGC

CTCAGTGAAGGTCCCCTGCAAGGCTTCTGGATACACCTTCACTAGCTATG

CTATGAATTGGGTGCGACAGGCCCCTGGACAAGGGCTTGAGTGGATGGGA

TGGATCAACACCAACACTGGGAACCCAACGTATGCCCAGGGCTTCACAGG

ACGGTTTGTCTTCTCCTTGGACACCTCTGTCAGCACGGCATATCTGCAGA

TCAGCAGCCTAAAGGCTGAGGACACTGCCGTGTATTACTGTGCGAGAGAG

GTAGTACCAGTTGCTATGAGGGTAACTCACTACTACTACGGTATGGACGT

CTGGGGCCAAGGGACCACGGTCACCGTCTCCTCAGCTAGCACCAA

The heavy chain amino acid sequence (SEQ ID NO: 10) of F4-465

MDWTWRILFLVAAATGAHSQVQLVQSGSELKKPGASVKVPCKASGYTFTS

YAMNWVRQAPGQGLEWMGWINTNTGNPTYAQGFTGRFVFSLDTSVSTAYL

QISSLKAEDTAVYYCAREVVPVAMRVTHYYYGMDVWGQGTTVTVSSAST

The light chain nucleic acid sequence (SEQ ID NO: 11) of F4-465

CTGGGTACGGTAACCGTCAGATCGCCTGGAGACGCCATCACAGATCTGCC

TCAGGAAGCAGCATCGGAGGTGCCTCAGCCATGGCATGGATCCCTCTCTT

CCTCGGCGTCCTTGTTTACTGCACAGGATCCGTGGCCTCCTATGAGCTGA

CTCAGCCACCCTCAGTGTCCGTGGCCCCAGGACAGACAGCCAGCATCACC

TGTTCTGGAGATAAATTGGGGGATAATTTTACTTGCTGGTATCAGCAGAA

GCCAGGCCAGTCCCCTGTGCTGGTCATCTTTCAGGATTGGAAGCGGCGCC

CAGGGATCCCTGCGCGATTCTCTGGCTCCAAGTCTGGGAACACAGCCACT

CTGACCATCAGCGGGACCCAGGCTATGGATGAGGCTGACTATTACTGTCA

GGCGTGGGACATCAGCACTGTGGTATTCGGCGGAGGGACCAAGCTGACCG

TCCTAGGTCAGCCCAAGGCTGCCCCCTCGGTCACTCTGTTCCCGCCCTCC

TCTGAGGAGCTTCAAGCCAACAAGGCCACACTGGTGTGTCTCATAAGTGA

CTTCTACCCGGGAGCCGTGACAGTGGCCTGGAAGGCAGATAGCAGCCCCG

TCAAGGCGGGAGTGGAGACCACCACACCCTCCAAACAAAGCAACAACAAG

TACGCGGCCAGCAGCTACCTGAGCCTGACGCCTGAGCAGTGGAAGTCCCA

CAGAAGCTACAGCTGCCAGGTCACGCATGAAGGGAGCACCGTGGAGAAGA

CAGTGGCCCCTACAGAATGTTCATGAATTCAGATCCGTTAACGGTTACCA

ACTACCTAGACTGGATTCGTGACCAACATA

The light chain amino acid sequence (SEQ ID NO: 12) of F4-465

MAWIPLFLGVLVYCTGSVASYELTQPPSVSVAPGQTASITCSGDKLGDNF

TCWYQQKPGQSPVLVIFQDWKRRPGIPARFSGSKSGNTATLTISGTQAMD

-continued

EADYYCQAWDISTVVFGGGTKLTVLGQPKAAPSVTLFPPSSEELQANKAT

LVCLISDFYPGAVTVAWKADSSPVKAGVETTTPSKQSNNKYAASSYLSLT

PEQWKSHRSYSCQVTHEGSTVEKTVAPTECS

The present inventors digested a DNA fragment comprising the heavy and light chains of 4D11 (having IgG4) that is an anti-CD40 antibody or 4D11PE (the 4D11 antibody gene) that is a mutant thereof with BglII and NheI, followed by purification. The resultant was integrated into an N5KG4PE vector (IDEC Pharmaceuticals). N5KG4PE has point mutations S228P and L235E in the IgG4 constant region. The culture supernatant thereof was transferred to a Protein A column (Amersham Biosciences) and eluted with a 0.1 M citric acid buffer (pH 2.7), followed by neutralization. Then, the pH was adjusted to 3.5, followed by incubation at 37° C. for 1 minute and again for 10 minutes. In such case, the resultant contains approximately 10% of the aggregate. However, the present inventors have found that an aggregate is not substantially produced in the case of 4D114D11G1 created by substituting the constant region of 4D11 with IgG1 (JP Patent Application No. 2003-431408). In order to specify the IgG1 region involved in inhibition of aggregate formation at a low pH, chimeric antibodies IgG [1/1/4/4], IgG[4/4/1/1], IgG[4/4/1/4], and IgG[4/4/4/1] were produced in the manner described below. ([1/1/4/4] indicates the CH1 domain derived from IgG1, the hinge region derived from IgG1, the CH2 domain derived from IgG4, and the CH3 domain derived from IgG4, and the same meaning is applied in the following similar descriptions.)

IgG[4/4/1/1] was subjected to a reaction with primers linkH: gggtacgtcctcacattcagtgatcag (SEQ ID NO: 13) and 24ch4: AGGGGTCCGGGAGATCATGAGAGTGTCCTT (SEQ ID NO: 14) at 98° C. for 1 second, 60° C. for 30 seconds, and 72° C. for 30 seconds for 15 cycles with the use of N5KG4PE (IDEC Pharmaceuticals) as a template. Meanwhile, IgG[4/4/1/1] was subjected to a reaction with primers 24ch3: AAGGACACTCTCATGATCTCCCGGACCCCT (SEQ ID NO: 15) and linkH2: tgatcatacgtagatatcacggc (SEQ ID NO: 16) at 98° C. for 1 second, 60° C. for 30 seconds, and 72° C. for 30 seconds for 15 cycles with the use of an antibody expression vector N5KG1-Val Lark (hereafter to be abbreviated as N5KG1; IDEC Pharmaceuticals) as a template. The amplified DNA fragments were purified using PCR purification kits. Equal amounts of the two types of purified DNA fragments were mixed together, followed by a reaction at 98° C. for 1 second, 60° C. for 30 seconds, and 72° C. for 30 seconds for 5 cycles. Then, primers linkH and linkH2 were added thereto, followed by a reaction for 15 cycles. The resulting amplified DNA fragment was cleaved with NheI and BamHI. Subsequently, the IgG1 constant region of an N5KG1 vector was substituted with the cleaved fragment. The thus obtained expression vector was designated as N5KG4411.

IgG[1/1/4/4] was subjected to a reaction with primers linkH: gggtacgtcctcacattcagtgatcag (SEQ ID NO: 13) and 24ch4: AGGGGTCCGGGAGATCATGAGAGTGTCCTT (SEQ ID NO: 14) at 98° C. for 1 second, 60° C. for 30 seconds, and 72° C. for 30 seconds for 15 cycles with the use of N5KG1 as a template. Meanwhile, IgG[1/1/4/4] was subjected to a reaction with primers 24ch3: AAGGACACTCTCATGATCTCCCGGACCCCT (SEQ ID NO: 15) and linkH2: tgatcatacgtagatatcacggc (SEQ ID NO: 16) at 98° C. for 1 second, 60° C. for 30 seconds, and 72° C. for 30 seconds for 15 cycles with the use of N5KG4PE as a template. The amplified DNA fragments were purified using PCR purification kits. Equal amounts of the two types of purified DNA fragments were mixed together, followed by a reaction at 98° C. for 1 second, 60° C. for 30 seconds, and 72° C. for 30 seconds for 5 cycles. Then, primers linkH and linkH2 were added thereto, followed by a reaction under the same conditions for 15 cycles. The resulting amplified DNA fragment was cleaved with NheI and BamHI. Subsequently, the IgG1 constant region of an N5KG1 vector was substituted with the cleaved fragment. The thus obtained expression vector was designated as N5KG1144.

IgG[4/4/1/4] was subjected to a reaction with primers linkH: gggtacgtcctcacattcagtgatcag (SEQ ID NO: 13) and CH3consR: GGTGTACACCTGTGGCTCTCGGGGCT-GCCC (SEQ ID NO: 17) at 98° C. for 1 second, 60° C. for 30 seconds, and 72° C. for 30 seconds for 15 cycles with the use of N5KG4411 produced as described above as a template. Meanwhile, IgG[4/4/1/4] was subjected to a reaction with primers CH3cons: GGGCAGCCCCGAGAGCCACA-GGTGTACACC (SEQ ID NO: 18) and linkH2: tgatcatacgtagatatcacggc (SEQ ID NO: 16) at 98° C. for 1 second, 60° C. for 30 seconds, and 72° C. for 30 seconds for 15 cycles with the use of N5KG4PE as a template. The amplified DNA fragments were purified using PCR purification kits. Equal amounts of the two types of purified DNA fragments were mixed together, followed by a reaction at 98° C. for 1 second, 60° C. for 30 seconds, and 72° C. for 30 seconds for 5 cycles. Then, primers linkH and linkH2 were added thereto, followed by a reaction under the same conditions for 15 cycles. The resulting amplified DNA fragment was cleaved with NheI and BamHI. Subsequently, the IgG1 constant region of an N5KG1 vector was substituted with the cleaved fragment. The thus obtained expression vector was designated as N5KG4414.

IgG[4/4/4/1] was subjected to a reaction with primers linkH: gggtacgtcctcacattcagtgatcag (SEQ ID NO: 13) and CH3consR: GGTGTACACCTGTGGCTCTCGGGGCT-GCCC (SEQ ID NO: 17) at 98° C. for 1 second, 60° C. for 30 seconds, and 72° C. for 30 seconds for 15 cycles with the use of N5KG4PE as a template. Meanwhile, IgG[4/4/1/4] was subjected to a reaction with primers CH3cons: GGGCAGCCCCGAGAGCCACAGGTGTACACC (SEQ ID NO: 18) and linkH2: tgatcatacgtagatatcacggc (SEQ ID NO: 16) at 98° C. for 1 second, 60° C. for 30 seconds, and 72° C. for 30 seconds for 15 cycles with the use of N5KG1 as a template. The amplified DNA fragments were purified using PCR purification kits. Equal amounts of the two types of purified DNA fragments were mixed together, followed by a reaction at 98° C. for 1 second, 60° C. for 30 seconds, and 72° C. for 30 seconds for 5 cycles. Then, primers linkH and linkH2 were added thereto, followed by a reaction under the same conditions for 15 cycles. The resulting amplified DNA fragment was cleaved with NheI and BamHI. Subsequently, the IgG1 constant region of an N5KG1 vector was substituted with the cleaved fragment. The thus obtained expression vector was designated as N5KG4441.

Each expression vector was cleaved with BglII and NheI. The light and heavy chain variable regions of 4D11 were inserted thereinto, resulting in the completion of the expression vectors.

Example 2: Expression and Purification of Chimeric Anti-CD40 Antibodies

The expression vector DNAs produced in Example 1 were adjusted with EndoFree Plasmid Kits (Qiagen) so as to be introduced into suspended 293 cells (Invitrogen life technology) with the use of a FreeStyle (registered trademark) 293 Expression System (Invitrogen life technology). Accordingly, culture supernatants each containing a different antibody were obtained as a result of transient expression. The culture supernatants (approximately 500 μg in terms of IgG) were each filtered with a membrane filter (pore size: 0.22 μm; MILLIPORE) and charged into a HiTrap rProtein A FF (column volume: 1 ml; Amersham Biosciences) affinity column used for antibody purification, followed by washing with PBS (−). Each resultant was eluted with a 20 mM citric acid buffer (pH 3.4) and collected into a tube containing a 200 mM phosphate buffer (pH 7.0). The aggregate content of each antibody sample after purification was 0% to 0.7%.

Example 3: Measurement of the Aggregate Contents in Antibody Solutions

The aggregate contents in the antibody solutions were analyzed with the use of a high-performance liquid chromatography apparatus (Shimadzu Corporation), a TSK-G3000 SW column (Tosoh Corporation), and 20 mM sodium phosphate and 500 mM NaCl (pH 7.0) as solvents. Peaks of antibody protein monomers and those of aggregates comprising a plurality of such monomers were identified by comparing elution positions derived from the antibody solutions and the elution position of a molecular weight marker (Cat No. 40403701; Oriental Yeast Co., Ltd.) used for gel filtration HPLC. The aggregate contents were measured based on the corresponding peak areas.

Example 4: Evaluation of Stabilities of Chimeric Anti-CD40 Antibodies

A buffer (60 μl; pH 2.7) comprising 200 mM sodium citrate and 50 mM NaCl was added to 300 μl of each antibody solution purified in the manner described in Example 2 such that the pH was adjusted to 3.5, followed by incubation at 37° C. for 10 minutes or 60 minutes. Each solution (150 μl) subjected to the pH-lowering treatment was neutralized with the addition of 37.5 μl of a 500 mM sodium phosphate buffer (pH 8.0). The aggregate contents of the antibody solutions subjected to the pH-lowering treatment were measured in the manner described in Example 3.

As a result, it was revealed that, when at least a CH3 domain is derived from IgG1 (IgG[4/4/1/1] or IgG[4/4/4/1]), the antibody has stability at low pH, which is comparable to the stability obtained when the entire constant region is IgG1 (table 1). Table 1 shows stabilities of IgG4/IgG1 chimeric antibodies at low pH.

TABLE 1

| Purified antibody | Aggregate (%) | |
| --- | --- | --- |
| | 10 minutes* | 60 minutes* |
| 4D11-G1 | 0.0 | 0.0 |
| 4D11-G4PE | 10.9 | 13.3 |
| 4D11-G[1/1/4/4] | 11.0 | 14.4 |
| 4D11-G[4/4/1/1] | 0.0 | 0.0 |
| 4D11-G[4/4/1/4] | 7.5 | 10.4 |
| 4D11-G[4/4/4/1] | 1.0 | 0.8 |

*Incubation time at low pH

Example 5: Production of Mutants (Mutant Antibodies) with Mutations in the Anti-CD40 Antibody Constant Region and Evaluation of the Inhibition of Aggregate Formation In order to further narrow down regions that contribute to inhibition of aggregate formation, 6 amino acid residues (at positions 355, 356, 358, 409, 419, and 445 indicated in the EU index as in Kabat et al.) with differences involving IgG1 and IgG4 in the CH3 domain were focused on. One of the amino acid residues of IgG4 was substituted with the corresponding amino acid residue of IgG1 such that mutants (Q355R (created by substituting a Gln residue at position 355 with Arg), E356D, M358L, R409K, E419Q, and L445P (created in the same manner as Q355R)) were produced. The mutants were produced with the use of the following: Q355R: CCTGCCCCCA TCCCGGGAGG AGATGAC-CAA G (SEQ ID NO: 19), E356D: CCATCCCA GGAC-GAGATG ACCAAGAAC (SEQ ID NO: 20), M358L: ATC-CCAGGAG GAGCTGACCA AGAACCAG (SEQ ID NO: 21), R409K: CTTCTTCCTC TACAGCAAGC TAAC-CGTGGA CAAG (SEQ ID NO: 22), E419Q: GAGCAG-GTGG CAGCAGGGGA ATGTCTTCTC (SEQ ID NO: 23), and L445P: CCTCTCCCTG TCTCCGGGTA AATGAG-GATC C (SEQ ID NO: 24). Different types of mutant DNAs each encoding a mutant with amino acid substitution in a constant region were prepared by a site-directed mutagenesis method with the use of a GeneEditor (registered trademark) in vitro Site-Directed Mutagenesis System (Promega) and a template DNA of the anti-CD40 antibody expression vector (described in WO02/088186 and JP Patent Application No. 2003-431408) that had been produced by inserting a DNA fragment comprising the heavy and light chains of the anti-CD40 antibody gene into an N5KG4PE vector (IDEC Pharmaceuticals). Mutagenic strands were synthesized by annealing mutagenic oligonucleotides of interest and a Selection Oligonucleotide provided in the above kit with template DNAs. Thereafter, based on the fact that mutants alone proliferate in the presence of a GeneEditor (registered trademark) Antibiotic Selection Mix, mutants were selected. More specifically, dsDNA templates were incubated under alkaline conditions (0.2 M NaOH and 0.2 mM EDTA (final concentration)) at room temperature for 5 minutes, followed by neutralization with the addition of 2M ammonium acetate (pH 4.6) in a manner such that the volume of ammonium acetate became 1/10 of that of the resulting solution. The resulting solution was recovered by ethanol precipitation. To the recovered alkaline-denatured template DNAs, mutagenic oligonucleotides (the sequences of 5'-end-phosphorylated oligonucleotides are shown in table 1) of interest, a Selection Oligonucleotide (5'-end-phosphorylated Top Select Oligo) used in relation with the new evolution of resistance to antibiotics, and an annealing buffer provided in the kit were added. The resultant was incubated at 75° C. for 5 minutes and slowly cooled down to 37° C. for annealing. For the purposes of synthesis and ligation of mutant strands, Synthesis 10× buffer, T4 DNA Polymerase, and T4 DNA ligase that are provided in the kit were added thereto, followed by a reaction at 37° C. for 90 minutes. Plasmid DNAs were prepared with the use of transformed *Escherichia coli* that had been transformed into BMH 71-18 mutS competent cells and cultured in the presence of a GeneEditor (registered trademark) Antibiotic Selection Mix. Further, with the use of such DNAs, JM109 competent cells were transformed. The resultants were seeded on an LB plate containing a GeneEditor (registered trademark) Antibiotic Selection Mix. Transformants that had been generated on the plate were cultured, followed by purification of plasmid DNAs. Then, the DNA nucleotide sequences were analyzed. Thus, expression vectors (N5KG4PE-4D11-Q355R, N5KG4PE-4D11-E356D, N5KG4PE-4D11-M358L, N5KG4PE-4D11-R409K, N5KG4PE-4D11-E419Q, and N5KG4PE-4D11-L445P) of anti-CD40 antibody mutants into each of which a desired amino acid mutation had been introduced were obtained. The obtained antibodies were expressed and purified in accordance with Example 2. Then, the stabilities at low pH were measured in accordance with Example 3.

As a result, among the 6 above mutants that had been produced, R409K (in which Arg at position 409 had been substituted with Lys) alone was found to be inhibited in terms of aggregate production at low pH (tables 2 and 3). Table 2 shows the stabilities at low pH in cases in which the amino acids of IgG1 were separately introduced into the CH3 domain of IgG4. Table 3 shows that the stabilities at low pH of R409K mutants are comparable to the stability of IgG1.

TABLE 2

| Purified antibody | Aggregate (%) | |
|---|---|---|
| | 10 minutes* | 60 minutes* |
| 4D11-G4PE[Q355R] | 9.0 | 12.2 |
| 4D11-G4PE[E356D] | 9.9 | 12.6 |
| 4D11-G4PE[M358L] | 8.5 | 11.5 |
| 4D11-G4PE[R409K] | 0.7 | 0.5 |
| 4D11-G4PE[E419Q] | 9.1 | 13.9 |
| 4D11-G4PE[L445P] | 10.6 | 11.8 |

*Incubation time at low pH

TABLE 3

| Purified antibody | Aggregate (%) | |
|---|---|---|
| | 10 minutes* | 60 minutes* |
| 4D11-G1 | 0.0 | 0.0 |
| 4D11-G4PE | 5.2 | 7.0 |
| 4D11-G[4/4/1/4] | 3.9 | 5.4 |
| 4D11-G[4/4/4/1] | 0.4 | 0.2 |
| 4D11-G4PE[R409K] | 0.0 | 0.0 |

*Incubation time at low pH

Example 6: Verification of Inhibition of Aggregate Formation at Low pH in Cases of Anti-CD40 Antibodies Such as KM281-1-10 and F4-465

Examination took place concerning the possibility of inhibition of aggregate formation under low pH conditions in cases in which F4-465 and KM281-1-10 antibodies, which, like 4D11, are anti-CD40 antibodies have IgG4 constant regions with R409K mutations. The light and heavy chain variable regions of N5KG4PE-4D11-R409K were digested with BglII and NheI so as to be cleaved. The cleaved regions were replaced with the light and heavy chain variable regions of KM281-1-10 or those of F4-465. The obtained antibodies were expressed and purified in accordance with Example 2. Then, the stabilities at low pH were measured in accordance with Example 3.

As a result, even in the cases of F4-465 and KM281-1-10, each of which has the variable region amino acid sequence differing from that of 4D11, a similar effect of amino acid substitution of R409K was confirmed (table 4). Table 4 shows that antibodies other than 4D11 have improved stability at low pH as a result of the R409K mutation.

TABLE 4

| Purified antibody | Aggregate | |
|---|---|---|
| | 10 minutes* | 60 minutes* |
| F4-465-G1 | 0.0 | 0.0 |
| F4-465-G4PE | 7.4 | 10.4 |
| F4-465-G4PE[R409K] | 0.0 | 0.0 |
| KM281-1-10-G1 | 0.0 | 0.0 |
| KM281-1-10-G4PE | 9.0 | 12.5 |
| KM281-1-10-G4PE[R409K] | 0.0 | 0.0 |

*Incubation time at low pH

Example 7: Binding Activity of Anti-CD40 Antibody to Ramos Cells

In order to examine whether or not the chimeric antibodies produced in Example 2 and the mutant antibodies obtained in Example 5 exert binding activities at levels that are comparable to the level of the original antibody, the binding activity with regard to Ramos[ATCC] cells that are expressed by CD40 was measured.

A Ramos cell line was suspended in a PBS staining buffer (SB) containing 0.1% $NaN_3$ and 2% FCS at a concentration of $2 \times 10^6$/ml. The cell suspension (100 μl/well) was dispensed into wells of a 96-well round-bottom plate (manufactured by Becton, Dickinson and Company). Each hybridoma culture supernatant (50 μl) was added thereto, followed by incubation at a temperature below freezing for 30 minutes. A human IgG1 antibody to human serum albumin as a negative control was adjusted to a concentration of 2 μg/ml in a hybridoma culture medium. The medium (50 μl) was added to the plate, followed by incubation at a temperature below freezing for 15 minutes. After washing the plate with SB, 50 μl of a 250-fold diluted R-PE fluorescently labeled anti-human antibody (Southern Biotechnology Associates, Inc.) was added to the plate, followed by incubation at a temperature below freezing for 15 minutes. After washing with SB twice, the plate was suspended in 300 to 500 μl of a FACS buffer, and the fluorescence intensity of each cell was measured using FACS (FACSort, FACScan, manufactured by Becton, Dickinson and Company).

Figure 1B:
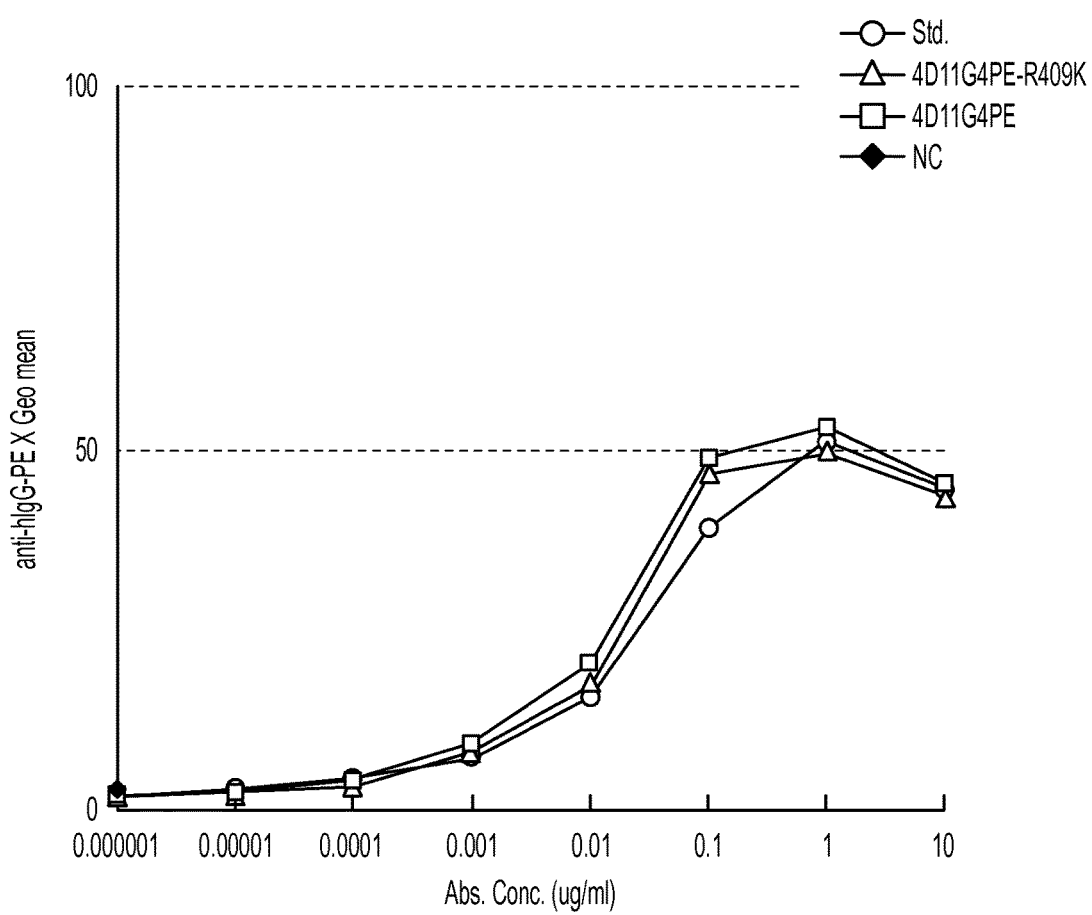
FIG. 1B shows results on the basis of binding activity, indicating that changes in a primary structure of the constant region cause no change in antibody-binding ability.
Figure 1C:
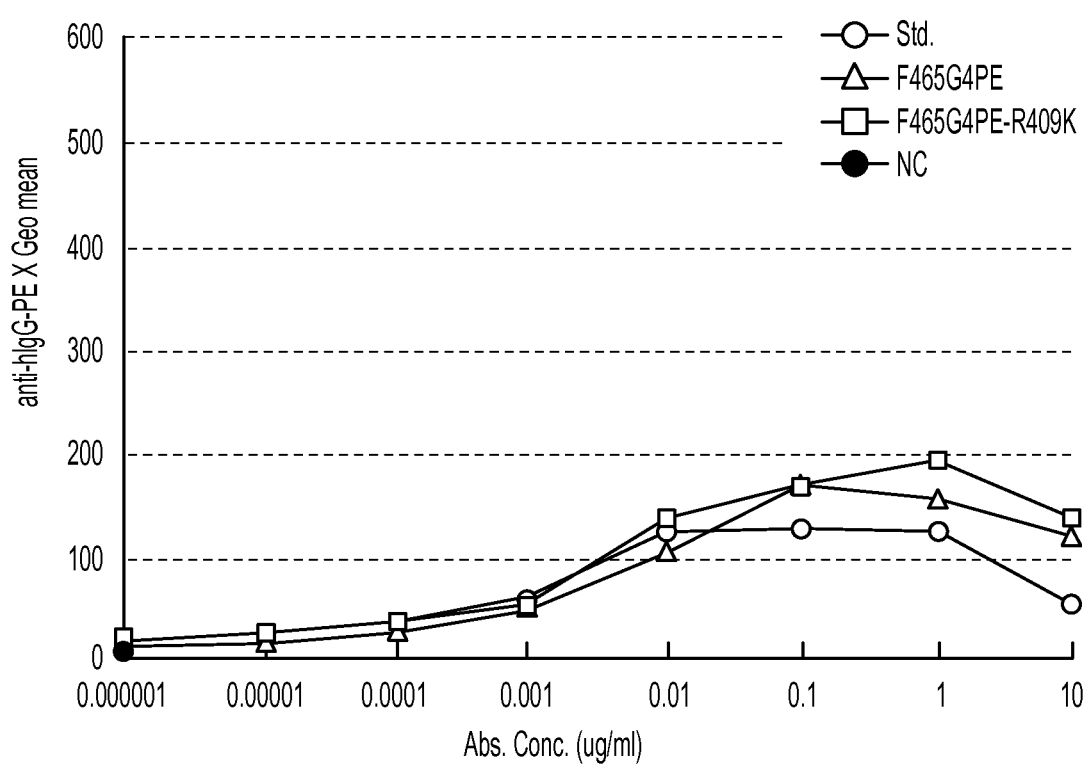
FIG. 1C shows results on the basis of binding activity, indicating that changes in a primary structure of the constant region cause no change in antibody-binding ability.
Figure 2A:
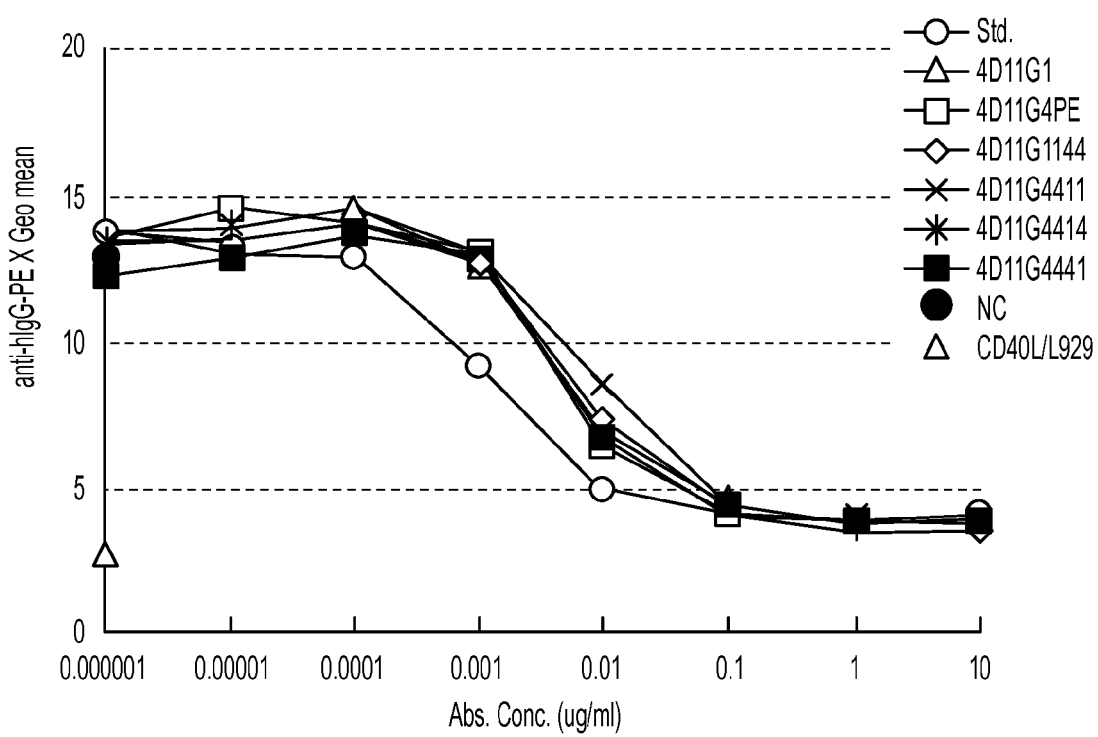
FIG. 2A shows results on the basis of antagonist activity (Ramos cellular assay), indicating that changes in a primary structure of the constant region cause no change in the antagonist activity of anti-CD40 antibody.
Figure 2B:
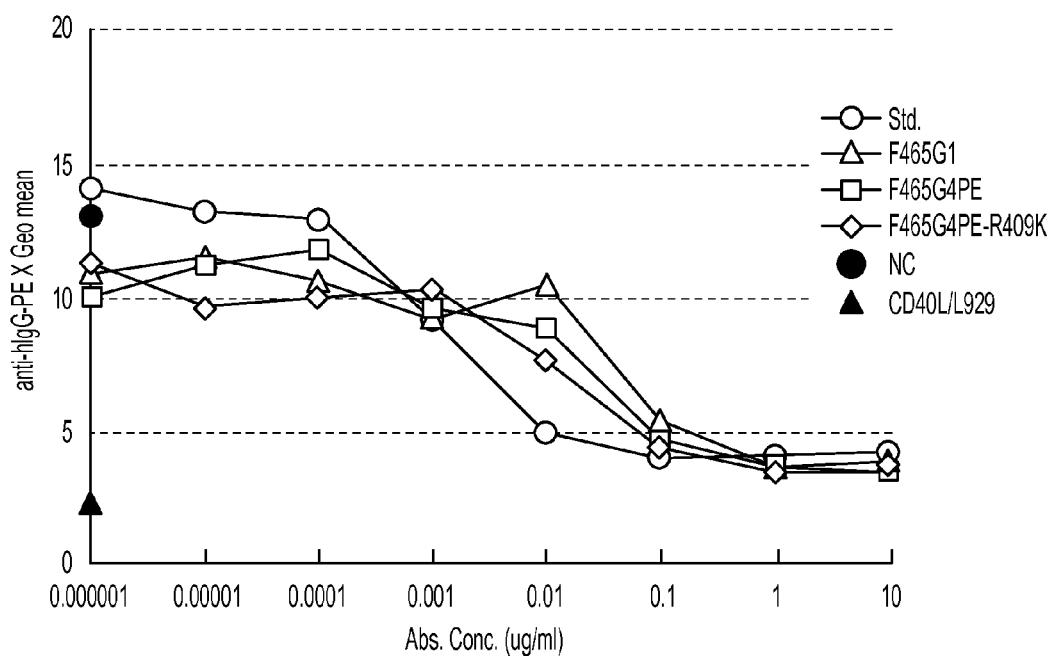
FIG. 2B shows results on the basis of antagonist activity (Ramos cellular assay), indicating that changes in a primary structure of the constant region cause no change in the antagonist activity of anti-CD40 antibody.
Figure 2C:
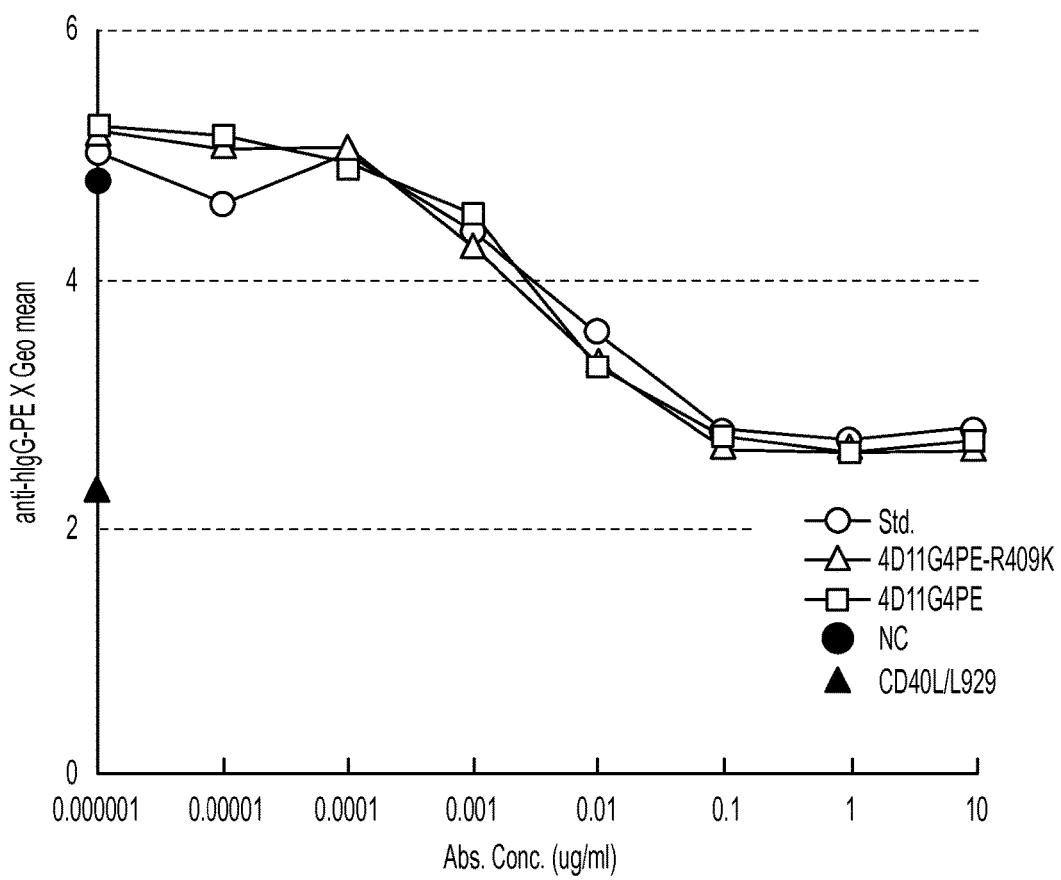
FIG. 2C shows results on the basis of antagonist activity (Ramos cellular assay), indicating that changes in a primary structure of the constant region cause no change in the antagonist activity of anti-CD40 antibody.
Figure 2D:
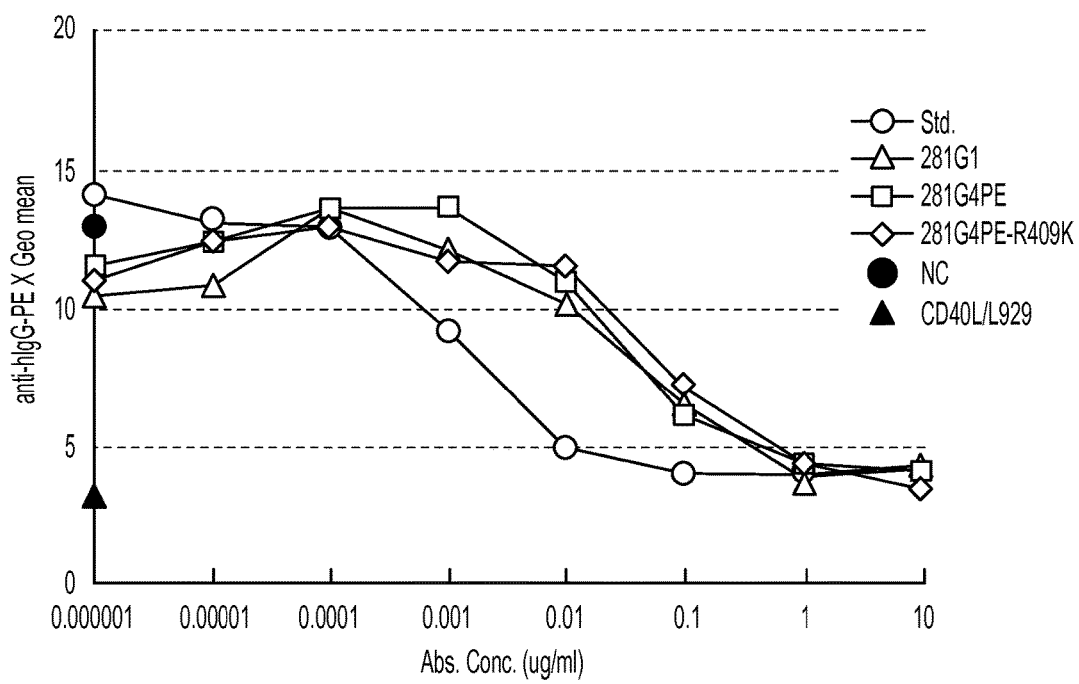
FIG. 2D shows results on the basis of antagonist activity (Ramos cellular assay), indicating that changes in a primary structure of the constant region cause no change in the antagonist activity of anti-CD40 antibody.

In the cases of the chimeric antibodies and the mutant antibodies, no changes in terms of binding activity were noted in the results (FIGS. 1A, 1B, and 1C).

Example 8: Inhibition of CD95 Expression by Anti-CD40 Antagonistic Antibody in Ramos Cells 4D11, F4-465, and KM281-1-10 are known as an antagonist antibody. Influences of structural changes in the constant region upon antagonist activities of such antibodies were examined. When a CD40 ligand is added to Ramos cells, an increased level of CD95 expression is observed. The antagonist activity of the antibody was evaluated based on an index that indicates the possibility of inhibition of increase in CD95 expression when the antibody is added in such case.

$1.0 \times 10^6$ cells/ml of a Ramos cell suspension was seeded on a 96-well plate at 50 μl/well. The culture supernatant or purified antibody was adjusted to 2 μg/ml in a medium, and the medium was added to the 96-well plate at 100 μl/well. 4 μg/ml of a soluble CD40 ligand (Alexis Corporation) and 4 μg/ml of an anti-FLAG antibody (M2, Sigma) were added to another medium, and the medium was added to the 96-well plate at 50 µl/well. After culturing overnight, cells were harvested, and an R-PE-labeled anti-CD95 antibody (Pharmingen NJ) was used for the cells. Analysis was carried out using FACS.

The results showed that structural changes in the constant region had caused no changes in the antagonist activities of the antibodies (FIGS. 2A, 2B, 2C, and 2D).

Example 9: Production of an IgG4PE Mutant with Substitution of 1 Amino Acid Residue at Position 409 in the CH3 Constant Region Since it was revealed that production of an IgG4 antibody aggregate at low pH is inhibited through amino acid substitution whereby an Arg residue at position 409 in the CH3 domain is substituted with Lys, IgG4 antibodies each having had the amino acid at such position substituted with a different one of the following 18 amino acid residues were produced (4D11-G4PE[R409A], 4D11-G4PE[R409D], 4D11-G4PE[R409E], 4D11-G4PE[R409F], 4D11-G4PE [R409G], 4D11-G4PE[R409H], 4D11-G4PE[R409I], 4D11-G4PE[R409L], 4D11-G4PE[R409M], 4D11-G4PE [R409N], 4D11-G4PE[R409I], 4D11-G4PE[R409Q], 4D11-G4PE[R409S], 4D11-G4PE[R409T], 4D11-G4PE[R409V], 4D11-G4PE[R409W], 4D11-G4PE[R409Y], and 4D11-G4PE[R409C]), followed by examination of stability at low pH. An expression vector of each mutant was produced by site-directed mutagenesis with the use of a GeneEditor (registered trademark) in vitro Site-Directed Mutagenesis System (Promega), as described in Example 5. DNA of an anti-CD40 antibody expression vector (described in WO02/088186 and JP Patent Application 2003-431408) was used as a template for site-directed mutagenesis. In addition, the 18 oligonucleotides presented below were used as oligonucleotides for mutagenesis (all the following synthetic DNAs were 5'-end-phosphorylated; each underlined base indicates a position into which amino acid mutation was introduced):

```
R409A production:
                                   (SEQ ID NO: 25)
CTTCTTCCTCTACAGCGCGCTAACCGTGGACAAG;

R409D production:
                                   (SEQ ID NO: 26)
CTTCTTCCTCTACAGCGACCTAACCGTGGACAAG;

R409E production:
                                   (SEQ ID NO: 27)
CTTCTTCCTCTACAGCGAGCTAACCGTGGACAAG;

R409F production:
                                   (SEQ ID NO: 28)
CTTCTTCCTCTACAGCTTCCTAACCGTGGACAAG;

R409G production:
                                   (SEQ ID NO: 29)
CTTCTTCCTCTACAGCGGGCTAACCGTGGACAAG;

R409H production:
                                   (SEQ ID NO: 30)
CTTCTTCCTCTACAGCCACCTAACCGTGGACAAG;

R409I production:
                                   (SEQ ID NO: 31)
CTTCTTCCTCTACAGCATCCTAACCGTGGACAAG;

R409L production:
                                   (SEQ ID NO: 32)
CTTCTTCCTCTACAGCCTGCTAACCGTGGACAAG;
```

```
-continued
R409M production:
                                   (SEQ ID NO: 33)
CTTCTTCCTCTACAGCATGCTAACCGTGGACAAG;

R409N production:
                                   (SEQ ID NO: 34)
CTTCTTCCTCTACAGCAACCTAACCGTGGACAAG;

R409P production:
                                   (SEQ ID NO: 35)
CTTCTTCCTCTACAGCCCGCTAACCGTGGACAAG;

R409Q production:
                                   (SEQ ID NO: 36)
CTTCTTCCTCTACAGCCAGCTAACCGTGGACAAG;

R409S production:
                                   (SEQ ID NO: 37)
CTTCTTCCTCTACAGCAGCCTAACCGTGGACAAG;

R409T production:
                                   (SEQ ID NO: 38)
CTTCTTCCTCTACAGCACGCTAACCGTGGACAAG;

R409V production:
                                   (SEQ ID NO: 39)
CTTCTTCCTCTACAGCGTGCTAACCGTGGACAAG;

R409W production:
                                   (SEQ ID NO: 40)
CTTCTTCCTCTACAGCTGGCTAACCGTGGACAAG;

R409Y production:
                                   (SEQ ID NO: 41)
CTTCTTCCTCTACAGCTACCTAACCGTGGACAAG;
and R409C production:
                                   (SEQ ID NO: 42)
CTTCTTCCTCTACAGCTGCCTAACCGTGGACAAG.
```

DNA nucleotide sequence analysis was carried out so as to select candidate plasmid DNAs of the mutant-antibody-expressing vectors obtained by site-directed mutagenesis and to confirm all of the total nucleotide sequences of the antibody-encoding regions. Thus, all the 18 types of expression vector of the mutants into each of which the desired amino acid mutation had been introduced.

Example 10: Evaluation of Inhibition of Aggregate Formation in Cases of Mutants with a Mutation of the Amino Acid Residue at Position 409 of an Anti-CD40 Antibody 4D11-G4PE Regarding 20 types of antibodies, including 18 types of mutants with a mutation of the amino acid residue at position 409, 4D11-G4PE, and 4D11-G4PE[R409K], an expression vector DNA of each antibody was transfected into a culture cell for protein expression in accordance with Example 2. Then, an antibody protein was purified from each culture supernatant. The purified antibodies were subjected to measurement of stability at low pH (37° C.) in accordance with Example 3. Table 5 shows the contents of aggregates that were generated when the antibody samples were treated at low pH for 60 minutes. As shown in table 5, no antibodies subjected to amino acid substitution experienced inhibition of aggregate formation at a comparable level to the case of 4D11-G4PE[R409K]. However, in the cases of 4D11-G4PE [R409M], 4D11-G4PE[R409T], and 4D11-G4PE[R409L], the aggregate contents were not more than 5%. Thus, in addition to the case in which an Arg residue at position 409 in the IgG4 antibody is substituted with Lys, it was confirmed that stability at low pH can be obtained in cases in which such amino acid residue is substituted with Met, Thr, or Leu.

TABLE 5

| Purified antibody | Aggregate (%) |
|---|---|
| 4D11-G4PE | 12.0 |
| 4D11-G4PE[R409K] | 0.8 |
| 4D11-G4PE[R409A] | 13.7 |
| 4D11-G4PE[R409D] | 10.6 |
| 4D11-G4PE[R409E] | 5.6 |
| 4D11-G4PE[R409F] | 7.9 |
| 4D11-G4PE[R409G] | 15.0 |
| 4D11-G4PE[R409H] | 11.4 |
| 4D11-G4PE[R409I] | 9.5 |
| 4D11-G4PE[R409L] | 4.1 |
| 4D11-G4PE[R409M] | 2.9 |
| 4D11-G4PE[R409N] | 7.1 |
| 4D11-G4PE[R409P] | 16.0 |
| 4D11-G4PE[R409Q] | 6.6 |
| 4D11-G4PE[R409S] | 9.8 |
| 4D11-G4PE[R409T] | 3.0 |
| 4D11-G4PE[R409V] | 5.4 |
| 4D11-G4PE[R409W] | 6.8 |
| 4D11-G4PE[R409Y] | 7.7 |
| 4D11-G4PE[R409C] | 10.4 |

All publications, patents, and patent applications cited herein are incorporated herein by reference in their entirety.

The invention claimed is:

1. A method of producing an antibody, said method comprising:
producing an expression vector encoding a heavy chain and a light chain of an antibody, wherein in said antibody, the amino acid residue at position 409 according to the EU index as in Kabat in a heavy chain constant region of human IgG4 is selected from the group consisting of lysine, threonine, methionine and leucine;
introducing the expression vector into a host cell;
culturing the host cell to thereby produce said antibody; and
recovering said antibody from the culture.

2. The method according to claim 1, wherein in said heavy chain constant region, the amino acid residue at position 228 according to the EU index as in Kabat is proline.

3. The method according to claim 1, wherein in said heavy chain constant region, the amino acid residue at position 235 according to the EU index as in Kabat is glutamic acid.

4. The method according to claim 1, wherein in said heavy chain constant region, the amino acid residue at position 228 according to the EU index as in Kabat is proline, and the amino acid residue at position 235 according to the EU index as in Kabat is glutamic acid.

5. The method according to claim 1, wherein the antibody has improved stability.

6. The method according to claim 1, wherein the antibody is a chimeric antibody, a humanized antibody or a human antibody.

7. A method of producing an antibody, said method comprising:
culturing a host cell containing an expression vector encoding a heavy chain and a light chain of an antibody, to thereby produce said antibody, wherein in said antibody, the amino acid residue at position 409 according to the EU index as in Kabat in a heavy chain constant region of human IgG4 is selected from the group consisting of lysine, threonine, methionine and leucine; and
recovering said antibody from the culture.

8. The method according to claim 7, wherein in said heavy chain constant region, the amino acid residue at position 228 according to the EU index as in Kabat is proline.

9. The method according to claim 7, wherein in said heavy chain constant region, the amino acid residue at position 235 according to the EU index as in Kabat is glutamic acid.

10. The method according to claim 7, wherein in said heavy chain constant region, the amino acid residue at position 228 according to the EU index as in Kabat is proline, and the amino acid residue at position 235 according to the EU index as in Kabat is glutamic acid.

11. The method according to claim 7, wherein the antibody has improved stability.

12. The method according to claim 7, wherein the antibody is a chimeric antibody, a humanized antibody or a human antibody.

13. An antibody in which the amino acid residue at position 409 according to the EU index in Kabat in a heavy chain constant region of human IgG4 is selected from the group consisting of lysine, threonine, methionine and leucine,
and wherein in said heavy chain constant region, the amino acid residue at position 228 according to the EU index in Kabat is proline, and/or the amino acid residue at position 235 according to the EU index in Kabat is glutamic acid.

14. The antibody according to claim 13, wherein the antibody has improved stability.

15. The antibody according to claim 13, wherein the antibody exhibits decreased aggregation.

16. The antibody according to claim 13, wherein the antibody is of a human IgG4 subclass.

17. The antibody according to claim 13, wherein the antibody is a chimeric antibody, a humanized antibody or a human antibody.

* * * * *

SEQUENCE LISTING

<160> NUMBER OF SEQ ID NOS: 48

<210> SEQ ID NO 1
<211> LENGTH: 462
<212> TYPE: DNA
<213> ORGANISM: Homo sapiens

<400> SEQUENCE: 1

```
atatgtcgac gagtcatgga tctcatgtgc aagaaaatga agcacctgtg gttcttcctc      60
ctgctggtgg cggctcccag atgggtcctg tcccagctgc agctgcagga gtcgggccca     120
ggactactga agccttcgga gaccctgtcc ctcacctgca ctgtctctgg cggctccatc     180
agcagtcctg gttactacgg gggctggatc cgccagcccc cagggaaggg gctggagtgg     240
attgggagta tctataaaag tgggagcacc taccacaacc cgtccctcaa gagtcgagtc     300
accatatccg tagacacgtc caagaaccag ttctccctga agctgagctc tgtgaccgcc     360
gcagacacgg ctgtgtatta ctgtacgaga cctgtagtac gatattttgg gtggttcgac     420
ccctggggcc agggaaccct ggtcaccgtc tcctcagcta gc                        462
```

<210> SEQ ID NO 2
<211> LENGTH: 149
<212> TYPE: PRT
<213> ORGANISM: Homo sapiens

<400> SEQUENCE: 2

```
Met Asp Leu Met Cys Lys Lys Met Lys His Leu Trp Phe Phe Leu Leu
 1               5                  10                  15
Leu Val Ala Ala Pro Arg Trp Val Leu Ser Gln Leu Gln Leu Gln Glu
            20                  25                  30
Ser Gly Pro Gly Leu Leu Lys Pro Ser Glu Thr Leu Ser Leu Thr Cys
        35                  40                  45
Thr Val Ser Gly Gly Ser Ile Ser Ser Pro Gly Tyr Tyr Gly Gly Trp
    50                  55                  60
Ile Arg Gln Pro Pro Gly Lys Gly Leu Glu Trp Ile Gly Ser Ile Tyr
65                  70                  75                  80
Lys Ser Gly Ser Thr Tyr His Asn Pro Ser Leu Lys Ser Arg Val Thr
                85                  90                  95
Ile Ser Val Asp Thr Ser Lys Asn Gln Phe Ser Leu Lys Leu Ser Ser
            100                 105                 110
Val Thr Ala Ala Asp Thr Ala Val Tyr Tyr Cys Thr Arg Pro Val Val
        115                 120                 125
Arg Tyr Phe Gly Trp Phe Asp Pro Trp Gly Gln Gly Thr Leu Val Thr
    130                 135                 140
```

Val Ser Ser Ala Ser
145

<210> SEQ ID NO 3
<211> LENGTH: 448
<212> TYPE: DNA
<213> ORGANISM: Homo sapiens

<400> SEQUENCE: 3

| | | |
|---|---|---|
| agatcttaag caagtgtaac aactcagagt acgcggggag acccactcag gacacagcat | 60 |
| ggacatgagg gtccccgctc agctcctggg gcttctgctg ctctggctcc caggtgccag | 120 |
| atgtgccatc cagttgaccc agtctccatc ctccctgtct gcatctgtag gagacagagt | 180 |
| caccatcact tgccgggcaa gtcagggcat tagcagtgct ttagcctggt atcagcagaa | 240 |
| accagggaaa gctcctaagc tcctgatcta tgatgcctcc aatttggaaa gtggggtccc | 300 |
| atcaaggttc agcggcagtg gatctgggac agatttcact ctcaccatca gcagcctgca | 360 |
| gcctgaagat tttgcaactt attactgtca acagtttaat agttacccga cgttcggcca | 420 |
| agggaccaag gtggaaatca aacgtacg | 448 |

<210> SEQ ID NO 4
<211> LENGTH: 130
<212> TYPE: PRT
<213> ORGANISM: Homo sapiens

<400> SEQUENCE: 4

Met Asp Met Arg Val Pro Ala Gln Leu Leu Gly Leu Leu Leu Trp
1               5                   10                  15

Leu Pro Gly Ala Arg Cys Ala Ile Gln Leu Thr Gln Ser Pro Ser
            20                  25                  30

Leu Ser Ala Ser Val Gly Asp Arg Val Thr Ile Thr Cys Arg Ala Ser
            35                  40                  45

Gln Gly Ile Ser Ser Ala Leu Ala Trp Tyr Gln Lys Pro Gly Lys
        50                  55                  60

Ala Pro Lys Leu Leu Ile Tyr Asp Ala Ser Asn Leu Glu Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Phe Ala Thr Tyr Tyr Cys Gln Gln
            100                 105                 110

Phe Asn Ser Tyr Pro Thr Phe Gly Gln Gly Thr Lys Val Glu Ile Lys
        115                 120                 125

Arg Thr
    130

<210> SEQ ID NO 5
<211> LENGTH: 481
<212> TYPE: DNA
<213> ORGANISM: Homo sapiens

<400> SEQUENCE: 5

| | | |
|---|---|---|
| ctgaacacag acccgtcgac tttgagagtc ctggacctcc tgtgcaagaa catgaaacat | 60 |
| ctgtggttct tccttctcct ggtggcagct cccagatggg tcctgtccca ggtgcagctg | 120 |
| caggagtcgg gcccaggact ggtgaagcct tcggagaccc tgtccctcac ctgcactgtc | 180 |
| tctggtggct ccatcagtgg ttactactgg agctggatcc ggcagccccc agggaaggga | 240 |

```
ctggagtgga ttgggtatat ctattacagt gggagcacca actacaatcc ctccctcaag    300
agtcgagtca ccatatcagt agacacgtcc aagaaccagt tctccctgaa gctgaattct    360
gtgaccgctg cggacacggc cgtgtattac tgtgcgagag ccccttgca cggtgactac     420 aaatggttcc accctgggg ccagggaacc ctggtcaccg tctcctcagc tagcaccaag     480
g                                                                    481

<210> SEQ ID NO 6
<211> LENGTH: 143
<212> TYPE: PRT
<213> ORGANISM: Homo sapiens

<400> SEQUENCE: 6

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Ser Gly Tyr Tyr Trp Ser Trp Ile Arg Gln Pro Pro Gly Lys Gly Leu
    50                  55                  60

Glu Trp Ile Gly Tyr Ile Tyr Tyr Ser Gly Ser Thr Asn Tyr Asn Pro
65                  70                  75                  80

Ser Leu Lys Ser Arg Val Thr Ile Ser Val Asp Thr Ser Lys Asn Gln
                85                  90                  95

Phe Ser Leu Lys Leu Asn Ser Val Thr Ala Ala Asp Thr Ala Val Tyr
            100                 105                 110

Tyr Cys Ala Arg Ala Pro Leu His Gly Asp Tyr Lys Trp Phe His Pro
        115                 120                 125

Trp Gly Gln Gly Thr Leu Val Thr Val Ser Ser Ala Ser Thr Lys
    130                 135                 140

<210> SEQ ID NO 7
<211> LENGTH: 430
<212> TYPE: DNA
<213> ORGANISM: Homo sapiens

<400> SEQUENCE: 7
tcacagatct gagctgctca gttaggaccc agagggaacc atggaaaccc cagcgcagct    60
tctcttcctc ctgctactct ggctcccaga taccaccgga gaaattgtgt tgacgcagtc    120
tccaggcacc ctgtctttgt ctccagggga agagccacc ctctcctgca gggccagtca    180
gagtgttagc agcagctact tagcctggta ccagcagaaa cctggccagg ctcccaggct    240
cctcatctat ggtgcatcca gcagggccac tggcatccca gacaggttca gtggcagtgg    300
gtctgggaca gacttcactc tcaccatcag cagactggag cctgaagatt ttgcagtgta    360
ttactgtcag cagtatggta gctcaccgat caccttcggc caagggacac gactggagat    420
caaacgtacg                                                           430

<210> SEQ ID NO 8
<211> LENGTH: 130
<212> TYPE: PRT
<213> ORGANISM: Homo sapiens

<400> SEQUENCE: 8

Met Glu Thr Pro Ala Gln Leu Leu Phe Leu Leu Leu Leu Trp Leu Pro
1               5                   10                  15
```

Asp Thr Thr Gly Glu Ile Val Leu Thr Gln Ser Pro Gly Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala
 50                  55                  60

Pro Arg Leu Leu Ile Tyr Gly Ala Ser Ser Arg Ala Thr Gly Ile Pro
 65                  70                  75                  80

Asp Arg Phe Ser Gly Ser Gly Ser Gly Thr Asp Phe Thr Leu Thr Ile
                 85                  90                  95

Ser Arg Leu Glu Pro Glu Asp Phe Ala Val Tyr Tyr Cys Gln Gln Tyr
            100                 105                 110

Gly Ser Ser Pro Ile Thr Phe Gly Gln Gly Thr Arg Leu Glu Ile Lys
            115                 120                 125

Arg Thr
    130

<210> SEQ ID NO 9
<211> LENGTH: 495
<212> TYPE: DNA
<213> ORGANISM: Homo sapiens

<400> SEQUENCE: 9
ctgaacacag acccgtcgac tacgcgggag accacagctc cacaccatgg actggacctg    60
gaggatccta ttcttggtgg cagcagcaac aggtgcccac tcccaggtgc agctggtgca   120
atctgggtct gagttgaaga agcctggggc ctcagtgaag gtccctgca aggcttctgg   180 atacaccttc actagctatg ctatgaattg ggtgcgacag gcccctgac aagggcttga   240 gtggatggga tggatcaaca ccaacactgg gaacccaacg tatgcccagg gcttcacagg   300
acggtttgtc ttctccttgg acacctctgt cagcacggca tatctgcaga tcagcagcct   360
aaaggctgag gacactgccg tgtattactg tgcgagagag gtagtaccag ttgctatgag   420
ggtaactcac tactactacg gtatggacgt ctggggccaa gggaccacgg tcaccgtctc   480
ctcagctagc accaa                                                    495

<210> SEQ ID NO 10
<211> LENGTH: 149
<212> TYPE: PRT
<213> ORGANISM: Homo sapiens

<400> SEQUENCE: 10

Met Asp Trp Thr Trp Arg Ile Leu Phe Leu Val Ala Ala Ala Thr Gly
 1               5                  10                  15

Ala His Ser Gln Val Gln Leu Val Gln Ser Gly Ser Glu Leu Lys Lys
            20                  25                  30

Pro Gly Ala Ser Val Lys Val Pro Cys Lys Ala Ser Gly Tyr Thr Phe
        35                  40                  45

Thr Ser Tyr Ala Met Asn Trp Val Arg Gln Ala Pro Gly Gln Gly Leu
 50                  55                  60

Glu Trp Met Gly Trp Ile Asn Thr Asn Thr Gly Asn Pro Thr Tyr Ala
 65                  70                  75                  80

Gln Gly Phe Thr Gly Arg Phe Val Phe Ser Leu Asp Thr Ser Val Ser
                 85                  90                  95

Thr Ala Tyr Leu Gln Ile Ser Ser Leu Lys Ala Glu Asp Thr Ala Val
            100                 105                 110

Tyr Tyr Cys Ala Arg Glu Val Val Pro Val Ala Met Arg Val Thr His
        115                 120                 125

Tyr Tyr Tyr Gly Met Asp Val Trp Gly Gln Gly Thr Thr Val Thr Val
130                 135                 140

Ser Ser Ala Ser Thr
145

<210> SEQ ID NO 11
<211> LENGTH: 830
<212> TYPE: DNA
<213> ORGANISM: Homo sapiens

<400> SEQUENCE: 11
ctgggtacgg taaccgtcag atcgcctgga gacgccatca cagatctgcc tcaggaagca      60
gcatcggagg tgcctcagcc atggcatgga tccctctctt cctcggcgtc cttgtttact     120
gcacaggatc cgtggcctcc tatgagctga ctcagccacc ctcagtgtcc gtggccccag     180
gacagacagc cagcatcacc tgttctggag ataaatttgg ggataatttt acttgctggt     240
atcagcagaa gccaggccag tcccctgtgc tggtcatctt tcaggattgg aagcggcgcc     300
cagggatccc tgcgcgattc tctggctcca agtctgggaa cacagccact ctgaccatca     360
gcgggaccca ggctatggat gaggctgact attactgtca ggcgtgggac atcagcactg     420
tggtattcgg cggagggacc aagctgaccg tcctaggtca gcccaaggct gccccctcgg     480
tcactctgtt cccgccctcc tctgaggagc ttcaagccaa caaggccaca ctggtgtgtc     540
tcataagtga cttctacccg ggagccgtga cagtggcctg gaaggcagat agcagccccg     600
tcaaggcggg agtggagacc accacaccct ccaaacaaag caacaacaag tacgcggcca     660
gcagctacct gagcctgacg cctgagcagt ggaagtccca cagaagctac agctgccagg     720
tcacgcatga agggagcacc gtggagaaga cagtggcccc tacagaatgt tcatgaattc     780
agatccgtta acggttacca actacctaga ctggattcgt gaccaacata             830

<210> SEQ ID NO 12
<211> LENGTH: 231
<212> TYPE: PRT
<213> ORGANISM: Homo sapiens

<400> SEQUENCE: 12

Met Ala Trp Ile Pro Leu Phe Leu Gly Val Leu Val Tyr Cys Thr Gly
1               5                   10                  15

Ser Val Ala Ser Tyr Glu Leu Thr Gln Pro Pro Ser Val Ser Val Ala
            20                  25                  30

Pro Gly Gln Thr Ala Ser Ile Thr Cys Ser Gly Asp Lys Leu Gly Asp
        35                  40                  45

Asn Phe Thr Cys Trp Tyr Gln Gln Lys Pro Gly Gln Ser Pro Val Leu
    50                  55                  60

Val Ile Phe Gln Asp Trp Lys Arg Arg Pro Gly Ile Pro Ala Arg Phe
65                  70                  75                  80

Ser Gly Ser Lys Ser Gly Asn Thr Ala Thr Leu Thr Ile Ser Gly Thr
                85                  90                  95

Gln Ala Met Asp Glu Ala Asp Tyr Tyr Cys Gln Ala Trp Asp Ile Ser
            100                 105                 110

Thr Val Val Phe Gly Gly Gly Thr Lys Leu Thr Val Leu Gly Gln Pro
        115                 120                 125

Lys Ala Ala Pro Ser Val Thr Leu Phe Pro Pro Ser Ser Glu Glu Leu

```
                130                 135                 140
Gln Ala Asn Lys Ala Thr Leu Val Cys Leu Ile Ser Asp Phe Tyr Pro
145                 150                 155                 160

Gly Ala Val Thr Val Ala Trp Lys Ala Asp Ser Ser Pro Val Lys Ala
                165                 170                 175

Gly Val Glu Thr Thr Thr Pro Ser Lys Gln Ser Asn Asn Lys Tyr Ala
                180                 185                 190

Ala Ser Ser Tyr Leu Ser Leu Thr Pro Glu Gln Trp Lys Ser His Arg
            195                 200                 205

Ser Tyr Ser Cys Gln Val Thr His Glu Gly Ser Thr Val Glu Lys Thr
        210                 215                 220

Val Ala Pro Thr Glu Cys Ser
225                 230

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 13
gggtacgtcc tcacattcag tgatcag                                    27

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 14
aggggtccgg gagatcatga gagtgtcctt                                 30

<210> SEQ ID NO 15
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 15
aaggacactc tcatgatctc ccggacccct                                 30

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 16
tgatcatacg tagatatcac ggc                                        23

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 17
ggtgtacacc tgtggctctc ggggctgccc                                 30
```

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 18
gggcagcccc gagagccaca ggtgtacacc           30

<210> SEQ ID NO 19
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 19
cctgccccca tcccgggagg agatgaccaa g          31

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 20
ccatcccagg acgagatgac caagaac              27

<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 21
atcccaggag gagctgacca agaaccag             28

<210> SEQ ID NO 22
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 22
cttcttcctc tacagcaagc taaccgtgga caag      34

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 23
gagcaggtgg cagcagggga atgtcttctc           30

<210> SEQ ID NO 24
<211> LENGTH: 31
<212> TYPE: DNA
<213> ORGANISM: Artificial Sequence
<220> FEATURE:

<223> OTHER INFORMATION: Description of Artificial Sequence:primer

<400> SEQUENCE: 24
cctctccctg tctccgggta aatgaggatc c                                31

<210> SEQ ID NO 25
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 25
cttcttcctc tacagcgcgc taaccgtgga caag                             34

<210> SEQ ID NO 26
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 26
cttcttcctc tacagcgacc taaccgtgga caag                             34

<210> SEQ ID NO 27
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 27
cttcttcctc tacagcgagc taaccgtgga caag                             34

<210> SEQ ID NO 28
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 28
cttcttcctc tacagcttcc taaccgtgga caag                             34

<210> SEQ ID NO 29
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 29
cttcttcctc tacagcgggc taaccgtgga caag                             34

<210> SEQ ID NO 30
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 30
cttcttcctc tacagccacc taaccgtgga caag                             34

```
<210> SEQ ID NO 31
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 31
cttcttcctc tacagcatcc taaccgtgga caag                              34

<210> SEQ ID NO 32
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 32
cttcttcctc tacagcctgc taaccgtgga caag                              34

<210> SEQ ID NO 33
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 33
cttcttcctc tacagcatgc taaccgtgga caag                              34

<210> SEQ ID NO 34
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 34
cttcttcctc tacagcaacc taaccgtgga caag                              34

<210> SEQ ID NO 35
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 35
cttcttcctc tacagcccgc taaccgtgga caag                              34

<210> SEQ ID NO 36
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 36
cttcttcctc tacagccagc taaccgtgga caag                              34

<210> SEQ ID NO 37
<211> LENGTH: 34
<212> TYPE: DNA
<213> ORGANISM: Artificial Sequence
<220> FEATURE:
<223> OTHER INFORMATION: Description of Artificial Sequence: Synthetic
```

<210> SEQ ID NO 37
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 37
cttcttcctc tacagcagcc taaccgtgga caag        34

<210> SEQ ID NO 38
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 38
cttcttcctc tacagcacgc taaccgtgga caag        34

<210> SEQ ID NO 39
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 39
cttcttcctc tacagcgtgc taaccgtgga caag        34

<210> SEQ ID NO 40
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 40
cttcttcctc tacagctggc taaccgtgga caag        34

<210> SEQ ID NO 41
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 41
cttcttcctc tacagctacc taaccgtgga caag        34

<210> SEQ ID NO 42
<211> LENGTH: 34
<212> TYPE: DNA
<213> ORGANISM: Artificial Sequence
<220> FEATURE:
<223> OTHER INFORMATION: Description of Artificial Sequence: Synthetic

<400> SEQUENCE: 42
cttcttcctc tacagctgcc taaccgtgga caag        34

<210> SEQ ID NO 43
<211> LENGTH: 1425
<212> TYPE: DNA
<213> ORGANISM: Homo sapiens

<400> SEQUENCE: 43
atggatctca tgtgcaagaa aatgaagcac ctgtggttct tcctcctgct ggtggcggct        60
cccagatggg tcctgtccca gctgcagctg caggagtcgg gcccaggact actgaagcct       120
tcggagaccc tgtccctcac ctgcactgtc tctggcggct ccatcagcag tcctggttac       180
tacgggggct ggatccgcca gccccccaggg aaggggctgg agtggattgg gagtatctat       240

-continued

```
aaaagtggga gcacctacca caacccgtcc ctcaagagtc gagtcaccat atccgtagac    300
acgtccaaga accagttctc cctgaagctg agctctgtga ccgccgcaga cacggctgtg    360
tattactgta cgagacctgt agtacgatat tttgggtggt tcgacccctg gggccaggga    420
accctggtca ccgtctcctc agctagcacc aagggcccat ccgtcttccc cctggcgccc    480
tgctccagga gcacctccga gcacagcc gccctgggct gcctggtcaa ggactacttc    540
cccgaaccgg tgacggtgtc gtggaactca ggcgccctga ccagcggcgt gcacaccttc    600
ccggctgtcc tacagtcctc aggactctac tccctcagca gcgtggtgac cgtgccctcc    660
agcagcttgg gcacgaagac ctacacctgc aacgtagatc acaagcccag caacaccaag    720
gtggacaaga gagttgagtc caaatatggt cccccatgcc catcatgccc agcacctgag    780
ttcctggggg gaccatcagt cttcctgttc ccccaaaac ccaaggacac tctcatgatc    840
tcccggaccc ctgaggtcac gtgcgtggtg gtggacgtga gccaggaaga ccccgaggtc    900
cagttcaact ggtacgtgga tggcgtggag gtgcataatg ccaagacaaa gccgcgggag    960
gagcagttca acagcacgta ccgtgtggtc agcgtcctca ccgtcctgca ccaggactgg   1020
ctgaacggca aggagtacaa gtgcaaggtc tccaacaaag gcctcccgtc ctccatcgag   1080
aaaaccatct ccaaagccaa agggcagccc cgagagccac aggtgtacac cctgccccca   1140
tcccaggagg agatgaccaa gaaccaggtc agcctgacct gcctggtcaa aggcttctac   1200
cccagcgaca tcgccgtgga gtgggagagc aatgggcagc cggagaacaa ctacaagacc   1260
acgcctcccg tgctggactc cgacggctcc ttcttcctct acagcaggct aaccgtggac   1320
aagagcaggt ggcaggaggg gaatgtcttc tcatgctccg tgatgcatga ggctctgcac   1380
aaccactaca cacagaagag cctctccctg tctctgggta aatga                   1425
```

<210> SEQ ID NO 44
<211> LENGTH: 474
<212> TYPE: PRT
<213> ORGANISM: Homo sapiens

<400> SEQUENCE: 44

```
Met Asp Leu Met Cys Lys Lys Met Lys His Leu Trp Phe Phe Leu Leu
  1               5                  10                  15
Leu Val Ala Ala Pro Arg Trp Val Leu Ser Gln Leu Gln Leu Gln Glu
             20                  25                  30
Ser Gly Pro Gly Leu Leu Lys Pro Ser Glu Thr Leu Ser Leu Thr Cys
         35                  40                  45
Thr Val Ser Gly Gly Ser Ile Ser Ser Pro Gly Tyr Tyr Gly Gly Trp
     50                  55                  60
Ile Arg Gln Pro Pro Gly Lys Gly Leu Glu Trp Ile Gly Ser Ile Tyr
 65                  70                  75                  80
Lys Ser Gly Ser Thr Tyr His Asn Pro Ser Leu Lys Ser Arg Val Thr
                 85                  90                  95
Ile Ser Val Asp Thr Ser Lys Asn Gln Phe Ser Leu Lys Leu Ser Ser
            100                 105                 110
Val Thr Ala Ala Asp Thr Ala Val Tyr Tyr Cys Thr Arg Pro Val Val
        115                 120                 125
Arg Tyr Phe Gly Trp Phe Asp Pro Trp Gly Gln Gly Thr Leu Val Thr
    130                 135                 140
Val Ser Ser Ala Ser Thr Lys Gly Pro Ser Val Phe Pro Leu Ala Pro
145                 150                 155                 160
```

```
Cys Ser Arg Ser Thr Ser Glu Ser Thr Ala Leu Gly Cys Leu Val
            165                 170                 175
Lys Asp Tyr Phe Pro Glu Pro Val Thr Val Ser Trp Asn Ser Gly Ala
            180                 185                 190
Leu Thr Ser Gly Val His Thr Phe Pro Ala Val Leu Gln Ser Ser Gly
            195                 200                 205
Leu Tyr Ser Leu Ser Ser Val Val Thr Val Pro Ser Ser Ser Leu Gly
        210                 215                 220
Thr Lys Thr Tyr Thr Cys Asn Val Asp His Lys Pro Ser Asn Thr Lys
225                 230                 235                 240
Val Asp Lys Arg Val Glu Ser Lys Tyr Gly Pro Pro Cys Pro Ser Cys
            245                 250                 255
Pro Ala Pro Glu Phe Leu Gly Gly Pro Ser Val Phe Leu Phe Pro Pro
            260                 265                 270
Lys Pro Lys Asp Thr Leu Met Ile Ser Arg Thr Pro Glu Val Thr Cys
        275                 280                 285
Val Val Val Asp Val Ser Gln Glu Asp Pro Glu Val Gln Phe Asn Trp
        290                 295                 300
Tyr Val Asp Gly Val Glu Val His Asn Ala Lys Thr Lys Pro Arg Glu
305                 310                 315                 320
Glu Gln Phe Asn Ser Thr Tyr Arg Val Val Ser Val Leu Thr Val Leu
            325                 330                 335
His Gln Asp Trp Leu Asn Gly Lys Glu Tyr Lys Cys Lys Val Ser Asn
            340                 345                 350
Lys Gly Leu Pro Ser Ser Ile Glu Lys Thr Ile Ser Lys Ala Lys Gly
        355                 360                 365
Gln Pro Arg Glu Pro Gln Val Tyr Thr Leu Pro Pro Ser Gln Glu Glu
        370                 375                 380
Met Thr Lys Asn Gln Val Ser Leu Thr Cys Leu Val Lys Gly Phe Tyr
385                 390                 395                 400
Pro Ser Asp Ile Ala Val Glu Trp Glu Ser Asn Gly Gln Pro Glu Asn
            405                 410                 415
Asn Tyr Lys Thr Thr Pro Pro Val Leu Asp Ser Asp Gly Ser Phe Phe
            420                 425                 430
Leu Tyr Ser Arg Leu Thr Val Asp Lys Ser Arg Trp Gln Glu Gly Asn
        435                 440                 445
Val Phe Ser Cys Ser Val Met His Glu Ala Leu His Asn His Tyr Thr
        450                 455                 460
Gln Lys Ser Leu Ser Leu Ser Leu Gly Lys
465                 470

<210> SEQ ID NO 45
<211> LENGTH: 708
<212> TYPE: DNA
<213> ORGANISM: Homo sapiens

<400> SEQUENCE: 45
atggacatga gggtccccgc tcagctcctg gggcttctgc tgctctggct cccaggtgcc      60
agatgtgcca tccagttgac ccagtctcca tcctccctgt ctgcatctgt aggagacaga     120
gtcaccatca cttgccgggc aagtcagggc attagcagtg ctttagcctg gtatcagcag     180
aaaccaggga agctcctaa gctcctgatc tatgatgcct ccaatttgga aagtggggtc     240
ccatcaaggt tcagcggcag tggatctggg acagatttca ctctcaccat cagcagcctg     300
cagcctgaag attttgcaac ttattactgt caacagttta atagttaccc gacgttcggc     360
```

```
caagggacca aggtggaaat caaacgtacg gtggctgcac catctgtctt catcttcccg    420
ccatctgatg agcagttgaa atctggaact gcctctgttg tgtgcctgct gaataacttc    480
tatcccagag aggccaaagt acagtggaag gtggataacg ccctccaatc gggtaactcc    540
caggagagtg tcacagagca ggacagcaag gacagcacct acagcctcag cagcaccctg    600
acgctgagca agcagactac gagaaacac aaagtctacg cctgcgaagt cacccatcag    660
ggcctgagct cgcccgtcac aaagagcttc aacaggggag agtgttga                708
```

<210> SEQ ID NO 46
<211> LENGTH: 235
<212> TYPE: PRT
<213> ORGANISM: Homo sapiens

<400> SEQUENCE: 46

```
Met Asp Met Arg Val Pro Ala Gln Leu Leu Gly Leu Leu Leu Leu Trp
 1               5                  10                  15

Leu Pro Gly Ala Arg Cys Ala Ile Gln Leu Thr Gln Ser Pro Ser Ser
             20                  25                  30

Leu Ser Ala Ser Val Gly Asp Arg Val Thr Ile Thr Cys Arg Ala Ser
         35                  40                  45

Gln Gly Ile Ser Ser Ala Leu Ala Trp Tyr Gln Gln Lys Pro Gly Lys
     50                  55                  60

Ala Pro Lys Leu Leu Ile Tyr Asp Ala Ser Asn Leu Glu Ser Gly Val
 65                  70                  75                  80

Pro Ser Arg Phe Ser Gly Ser Gly Ser Gly Thr Asp Phe Thr Leu Thr
                 85                  90                  95

Ile Ser Ser Leu Gln Pro Glu Asp Phe Ala Thr Tyr Tyr Cys Gln Gln
            100                 105                 110

Phe Asn Ser Tyr Pro Thr Phe Gly Gln Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235
```

<210> SEQ ID NO 47
<211> LENGTH: 1425
<212> TYPE: DNA
<213> ORGANISM: Homo sapiens

<400> SEQUENCE: 47

```
atggatctca tgtgcaagaa aatgaagcac ctgtggttct tcctcctgct ggtggcggct     60
cccagatggg tcctgtccca gctgcagctg caggagtcgg gcccaggact actgaagcct    120
tcggagaccc tgtccctcac ctgcactgtc tctggcggct ccatcagcag tcctggttac    180
```

```
tacgggggct ggatccgcca gcccccaggg aagggggctgg agtggattgg gagtatctat    240
aaaagtggga gcacctacca caacccgtcc ctcaagagtc gagtcaccat atccgtagac    300
acgtccaaga accagttctc cctgaagctg agctctgtga ccgccgcaga cacggctgtg    360
tattactgta cgagacctgt agtacgatat tttgggtggt tcgaccccctg ggccaggga    420 accctggtca ccgtctcctc agctagcacc aaggggccat ccgtcttccc cctggcgccc    480
tgctccagga gcacctccga gagcacagcc gccctgggct gcctggtcaa ggactacttc    540
cccgaaccgg tgacggtgtc gtggaactca ggcgccctga ccagcggcgt gcacaccttc    600
ccggctgtcc tacagtcctc aggactctac tccctcagca gcgtggtgac cgtgccctcc    660
agcagcttgg gcacgaagac ctacacctgc aacgtagatc acaagcccag caacaccaag    720
gtggacaaga gagttgagtc caaatatggt cccccatgcc caccatgccc agcacctgag    780
ttcgaggggg gaccatcagt cttcctgttc cccccaaaac ccaaggacac tctcatgatc    840
tcccggaccc ctgaggtcac gtgcgtggtg gtggacgtga gccaggaaga ccccgaggtc    900
cagttcaact ggtacgtgga tggcgtggag gtgcataatg ccaagacaaa gccgcgggag    960
gagcagttca acagcacgta ccgtgtggtc agcgtcctca ccgtcctgca ccaggactgg    1020
ctgaacggca aggagtacaa gtgcaaggtc tccaacaaag gcctcccgtc ctccatcgag    1080
aaaaccatct ccaaagccaa agggcagccc cgagagccac aggtgtacac cctgccccca    1140
tcccaggagg agatgaccaa gaaccaggtc agcctgacct gcctggtcaa aggcttctac    1200
cccagcgaca tcgccgtgga gtgggagagc aatgggcagc cggagaacaa ctacaagacc    1260
acgcctcccg tgctggactc cgacggctcc ttcttcctct acagcaagct aaccgtggac    1320
aagagcaggt ggcaggaggg gaatgtcttc tcatgctccg tgatgcatga ggctctgcac    1380
aaccactaca cacagaagag cctctcccctg tctctgggta aatga    1425
```

<210> SEQ ID NO 48
<211> LENGTH: 474
<212> TYPE: PRT
<213> ORGANISM: Homo sapiens

<400> SEQUENCE: 48

```
Met Asp Leu Met Cys Lys Lys Met Lys His Leu Trp Phe Phe Leu Leu
 1               5                  10                  15

Leu Val Ala Ala Pro Arg Trp Val Leu Ser Gln Leu Gln Leu Gln Glu
            20                  25                  30

Ser Gly Pro Gly Leu Leu Lys Pro Ser Glu Thr Leu Ser Leu Thr Cys
        35                  40                  45

Thr Val Ser Gly Gly Ser Ile Ser Ser Pro Gly Tyr Tyr Gly Gly Trp
    50                  55                  60

Ile Arg Gln Pro Pro Gly Lys Gly Leu Glu Trp Ile Gly Ser Ile Tyr
65                  70                  75                  80

Lys Ser Gly Ser Thr Tyr His Asn Pro Ser Leu Lys Ser Arg Val Thr
                85                  90                  95

Ile Ser Val Asp Thr Ser Lys Asn Gln Phe Ser Leu Lys Leu Ser Ser
            100                 105                 110

Val Thr Ala Ala Asp Thr Ala Val Tyr Tyr Cys Thr Arg Pro Val Val
        115                 120                 125

Arg Tyr Phe Gly Trp Phe Asp Pro Trp Gly Gln Gly Thr Leu Val Thr
    130                 135                 140

Val Ser Ser Ala Ser Thr Lys Gly Pro Ser Val Phe Pro Leu Ala Pro
```

-continued

```
145                 150                 155                 160
Cys Ser Arg Ser Thr Ser Glu Ser Thr Ala Ala Leu Gly Cys Leu Val
            165                 170                 175
Lys Asp Tyr Phe Pro Glu Pro Val Thr Val Ser Trp Asn Ser Gly Ala
            180                 185                 190
Leu Thr Ser Gly Val His Thr Phe Pro Ala Val Leu Gln Ser Ser Gly
            195                 200                 205
Leu Tyr Ser Leu Ser Ser Val Val Thr Val Pro Ser Ser Ser Leu Gly
            210                 215                 220
Thr Lys Thr Tyr Thr Cys Asn Val Asp His Lys Pro Ser Asn Thr Lys
225                 230                 235                 240
Val Asp Lys Arg Val Glu Ser Lys Tyr Gly Pro Pro Cys Pro Pro Cys
            245                 250                 255
Pro Ala Pro Glu Phe Glu Gly Gly Pro Ser Val Phe Leu Phe Pro Pro
            260                 265                 270
Lys Pro Lys Asp Thr Leu Met Ile Ser Arg Thr Pro Glu Val Thr Cys
            275                 280                 285
Val Val Val Asp Val Ser Gln Glu Asp Pro Glu Val Gln Phe Asn Trp
            290                 295                 300
Tyr Val Asp Gly Val Glu Val His Asn Ala Lys Thr Lys Pro Arg Glu
305                 310                 315                 320
Glu Gln Phe Asn Ser Thr Tyr Arg Val Val Ser Val Leu Thr Val Leu
            325                 330                 335
His Gln Asp Trp Leu Asn Gly Lys Glu Tyr Lys Cys Lys Val Ser Asn
            340                 345                 350
Lys Gly Leu Pro Ser Ser Ile Glu Lys Thr Ile Ser Lys Ala Lys Gly
            355                 360                 365
Gln Pro Arg Glu Pro Gln Val Tyr Thr Leu Pro Pro Ser Gln Glu Glu
            370                 375                 380
Met Thr Lys Asn Gln Val Ser Leu Thr Cys Leu Val Lys Gly Phe Tyr
385                 390                 395                 400
Pro Ser Asp Ile Ala Val Glu Trp Glu Ser Asn Gly Gln Pro Glu Asn
            405                 410                 415
Asn Tyr Lys Thr Thr Pro Pro Val Leu Asp Ser Asp Gly Ser Phe Phe
            420                 425                 430
Leu Tyr Ser Lys Leu Thr Val Asp Lys Ser Arg Trp Gln Glu Gly Asn
            435                 440                 445
Val Phe Ser Cys Ser Val Met His Glu Ala Leu His Asn His Tyr Thr
450                 455                 460
Gln Lys Ser Leu Ser Leu Ser Leu Gly Lys
465                 470
```